(12) United States Patent
Ward et al.

(10) Patent No.: US 6,657,045 B1
(45) Date of Patent: Dec. 2, 2003

(54) GP40 AND USES THEREOF

(75) Inventors: Honorine Ward, Lexington, MA (US); David Hamer, Cambridge, MA (US); Gerald Keusch, Lexington, MA (US); Ana Maria Cevallos, Coyoacan (MX)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 09/545,216

(22) Filed: Apr. 7, 2000

(51) Int. Cl.[7] .......................... C07K 16/00; C07K 1/00
(52) U.S. Cl. .................................. 530/324; 530/350
(58) Field of Search ............................ 530/300, 324, 530/350; 435/71.1

(56) References Cited

PUBLICATIONS

Spano et al., Molecular Cloning and expression ananlysis of a *Cryptosporidium parvum* gene encoding a new member of the thrombospondin family, *Molecular and Biochemical Parasitology*, 92:147–162 (1998).

Strong et al., Cloning and Sequence Analysis of a Highly Polymorphic *Cryptosporidium parvum* Gene Encoding a 60–Kilodalton Glycoprotein and characterization of Its 15–and 45–Kilodalton Zoite Surface Antigen Products, *Infection and Immunity*, 68, No. 7:4117–4134 (Jul. 2000).
Copy of International Search Report dated Nov. 16, 2001.
Arrowood et al. *J Parasitol.* 73:314–319, 1987.
Barnes et al., Mol. Biochem. Parasitol. 96:93–110, 1998.
Gut et al., *J. Eukaryot. Microbiol,* 41:42S–43S, 1994.
Petersen et al., *Infection & Immun.* 60:5132–5138, 1992.
Tzipori et al., *Adv Parasitol.* 40:5–36, 1998.
Tzipori et al. *Res. Vet. Sci.* 31:358–368, 1981.
Verdon et al., *J. Infect Dis.* 175:1268–1672, 1997.
Ward et al., *Adv Parqsitol.* 40:151–185, 1998.

*Primary Examiner*—Mark Navarro
(74) *Attorney, Agent, or Firm*—Fish & Richardson P.C.

(57) ABSTRACT

The present invention relates to a gene encoding a novel protein, gp40. gp40 polypeptides play a role in mediating host-parasite interactions. Described herein are isolated and antisense nucleic acids molecules, recombinant expression vectors and host cells. Diagnostic, screening and therapeutic methods utilizing the compositions of the invention are also provided.

2 Claims, 10 Drawing Sheets

ATGAGATTGTCGCTCATTATCGTATTACTCTCCGTTATAGTCTCCGCTGTATTCTCAGCC
CCAGCCGTTCCACTCAGAGGAACTTTAAAGGATGTTCCTGTTGAGGGCTCATCATCGTCA
TCGTCATCATCATCATCATCATCATCATCATCATCATCATCATCAACATCAACCGTCGCA
CCAGCAAATAAGGCAAGAACTGGAGAAGACGCAGAAGGCAGTCAAGATTCTAGTGGTACT
GAAGCTTCTGGTAGCCAGGGTTCTGAAGAGGAAGGTAGTGAAGACGATGGCCAAACTAGT
GCTGCTTCCCAACCCACTACTCCAGCTCAAAGTGAAGGCGCAACTACCGAAACCATAGAA
GCTACTCCAAAAGAAGAATGCGGCACTTCATTTGTAATGTGGTTCGGAGAAGGTACCCCA
GCTGCGACATTGAAGTGTGGTGCCTACACTATCGTCTATGCACCTATAAAAGACCAAACA
GATCCCGCACCAAGATATATCTCTGGTGAAGTTACATCTGTAACCTTTGAAAAGAGTGAT
AATACAGTTAAAATCAAGGTTAACGGTCAGGATTTCAGCACTCTCTCTGCTAATTCAAGT
AGTCCAACTGAAAATGGCGGATCTGCGGGTCAGGCTTCATCAAGATCAAGAAGATCACTC
TCAGAGGAAACCAGTGAAGCTGCTGCAACCGTCGATTTGTTTGCCTTTACCCTTGATGGT
GGTAAAAGAATTGAAGTGGCTGTACCAAACGTCGAAGATGCATCTAAAAGAGACAAGTAC
AGTTTGGTTGCAGACGATAAACCTTTCTATACCGGCGCAAACAGCGGCACTACCAATGGT
GTCTACAGGTTGAATGAGAACGGAGACTTGGTTGATAAGGACAACACAGTTCTTTTGAAG
GATGCTGGTTCCTCTGCTTTTGGACTCAGATACATCGTTCCTTCCGTTTTTGCAATCTTT
GCAGCCTTATTCGTGTTGTAA; (SEQ ID NO: 1)

FIG. 1

ATGAGATTGTCGCTCATTATCGTATTACTCTCCGTTATAGTCTCCGCTGTATTCTCAGCCCCAG
CCGTTCCACTCAGAGGAACTTTAAAGGATGTTCCTGTTGAGGGCTCATCATCGTCATCGTCATC
ATCATCATCATCATCATCATCATCATCATCATCATCAACATCAACCGTCGCACCAGCAAATAA
GGCAAGAACTGGAGAAGACGCAGAAGGCAGTCAAGATTCTAGTGGTACTGAAGCTTCTGGTA
GCCAGGGTTCTGAAGAGGAAGGTAGTGAAGACGATGGCCAAACTAGTGCTGCTTCCCAACCC
ACTACTCCAGCTCAAAGTGAAGGCGCAACTACCGAAACCATAGAAGCTACTCCAAAAGAAGA
ATGCGGCACTTCATTTGTAATGTGGTTCGGAGAAGGTACCCCAGCTGCGACATTGAAGTGTGG
TGCCTACACTATCGTCTATGCACCTATAAAAGACCAAACAGATCCCGCACCAAGATATATCTC
TGGTGAAGTTACATCTGTAACCTTTGAAAAGAGTGATAATACAGTTAAAATCAAGGTTAACGG
TCAGGATTTCAGCACTCTCTCTGCTAATTCAAGTAGTCCAACTGAAAATGGCGGATCTGCGGG
TCAGGCTTCATCAAGATCAAGAAGATCACTCTCAGAG (SEQ ID NO: 3)

FIG. 2

MRLSLIIVLLSVIVSAVFSAPAVPLRGTLKDVPVEGSSSSSSSSSSSSSSSSSSSTSTVAPANKARTGE
DAEGSQDSSGTEASGSQGSEEEGSEDDGQTSAASQPTTPAQSEGATTETIEATPKEECGTSFVMWF
GEGTPAATLKCGAYTIVYAPIKDQTDPAPRYISGEVTSVTFEKSDNTVKIKVNGQDFSTLSANSSSP
TENGGSAGQASSRSRRSLSE (SEQ ID NO: 2)

FIG. 3

```
GAAACCAGTGAAGCTGCTGCAACCGTCGATTTGTTTGCCTTTACCCTTGATGGTGGTAAAAGA
ATTGAAGTGGCTGTACCAAACGTCGAAGATGCATCTAAAAGAGACAAGTACAGTTTGGTTGC
AGACGATAAACCTTTCTATACCGGCGCAAACAGCGGCACTACCAATGGTGTCTACAGGTTGAA
TGAGAACGGAGACTTGGTTGATAAGGACAACACAGTTCTTTTGAAGGATGCTGGTTCCTCTGC
TTTTGGACTCAGATACATCGTTCCTTCCGTTTTTGCAATCTTTGCAGCCTTATTCGTGTTGTAA
(SEQ ID NO: 7)
```

FIG. 4

ETSEAAATVDLFAFTLDGGKRIEVAVPNVEDASKRDKYSLVADDKPFYTGANSGTTNGVYRLNE
NGDLVDKDNTVLLKDAGSSAFGLRYIVPSVFAIFAALFVL* (SEQ ID NO: 8)

FIG. 5

```
                                                                                            *
                                                        *                       *        *****
             ▽                     *                  **                      **         SSSSS
           * *                   *****                **                      **         VEGSS
         * * *                  *SSSSS                **                      **         KDVP
        ***S*S                 *SSSSSS               **S                     **S         LRGT
       *SSS*S                ***SSSSSS              **SS                    **SS         VPL
      *SSSSS                 *SSSSSSS             **SSS                    **SSS         APA
     *SSSSS                ****SSSSSS            **SSSS                   **SSSS         FS
```

MRLSLIIVLLSVIVSAVFSAPAVPLRGTLKDVPVEGSSSSS

SSSSSSSSSSSSSSSSSSSTSTVAPANKARTGEDAEGSQDSSGTEA

SGSQGSEEGSEDDGQTSAASQPTTPAQSEGATTETIEATP

KEECGTSFVMWFGEGTPAATLKCGAYTIVYAPIKDQTDPAP

RYISGEVTSVTFEKSDNTVKIKVNGQDFSTLSA NSSS PTEN

GGSAGQASSRSRRSLSEETSEAAATVDLFAFTLDGGKRIEV

AVPNVEDASKRDKYSLVADDKPFYTGANSGTTNGVYRLNEN

GDLVDKDNTVLLKDAGSSAFGLRYIVPSVFAIFAALFVL (SEQ ID NO: 6)

SEQUENCE LISTING

<160> NUMBER OF SEQ ID NOS: 8

<210> SEQ ID NO 1
<211> LENGTH: 981
<212> TYPE: DNA
<213> ORGANISM: Cryptosporidium parvum

<220> FEATURE:
<221> NAME/KEY: CDS
<222> LOCATION: (1)...(978)

<400> SEQUENCE: 1

| | | | | | | | | | | | | | | | | |
|---|---|---|---|---|---|---|---|---|---|---|---|---|---|---|---|---|
| atg | aga | ttg | tcg | ctc | att | atc | gta | tta | ctc | tcc | gtt | ata | gtc | tcc | gct | 48 |
| Met | Arg | Leu | Ser | Leu | Ile | Ile | Val | Leu | Leu | Ser | Val | Ile | Val | Ser | Ala | |
| 1 | | | | 5 | | | | | 10 | | | | | 15 | | |
| gta | ttc | tca | gcc | cca | gcc | gtt | cca | ctc | aga | gga | act | tta | aag | gat | gtt | 96 |
| Val | Phe | Ser | Ala | Pro | Ala | Val | Pro | Leu | Arg | Gly | Thr | Leu | Lys | Asp | Val | |
| | | | 20 | | | | | 25 | | | | | 30 | | | |
| cct | gtt | gag | ggc | tca | tca | tcg | tca | tcg | tca | tca | tca | tca | tca | tca | tca | 144 |
| Pro | Val | Glu | Gly | Ser | Ser | Ser | Ser | Ser | Ser | Ser | Ser | Ser | Ser | Ser | Ser | |
| | | | 35 | | | | | 40 | | | | | 45 | | | |
| tca | tca | tca | tca | tca | tca | tca | aca | tca | acc | gtc | gca | cca | gca | aat | aag | 192 |
| Ser | Ser | Ser | Ser | Ser | Ser | Ser | Thr | Ser | Thr | Val | Ala | Pro | Ala | Asn | Lys | |
| | 50 | | | | | 55 | | | | | 60 | | | | | |
| gca | aga | act | gga | gaa | gac | gca | gaa | ggc | agt | caa | gat | tct | agt | ggt | act | 240 |
| Ala | Arg | Thr | Gly | Glu | Asp | Ala | Glu | Gly | Ser | Gln | Asp | Ser | Ser | Gly | Thr | |
| 65 | | | | | 70 | | | | | 75 | | | | | 80 | |
| gaa | gct | tct | ggt | agc | cag | ggt | tct | gaa | gag | gaa | ggt | agt | gaa | gac | gat | 288 |
| Glu | Ala | Ser | Gly | Ser | Gln | Gly | Ser | Glu | Glu | Glu | Gly | Ser | Glu | Asp | Asp | |
| | | | | 85 | | | | | 90 | | | | | 95 | | |
| ggc | caa | act | agt | gct | gct | tcc | caa | ccc | act | act | cca | gct | caa | agt | gaa | 336 |
| Gly | Gln | Thr | Ser | Ala | Ala | Ser | Gln | Pro | Thr | Thr | Pro | Ala | Gln | Ser | Glu | |
| | | | 100 | | | | | 105 | | | | | 110 | | | |
| ggc | gca | act | acc | gaa | acc | ata | gaa | gct | act | cca | aaa | gaa | gaa | tgc | ggc | 384 |
| Gly | Ala | Thr | Thr | Glu | Thr | Ile | Glu | Ala | Thr | Pro | Lys | Glu | Glu | Cys | Gly | |
| | | | | 115 | | | | | 120 | | | | | 125 | | |
| act | tca | ttt | gta | atg | tgg | ttc | gga | gaa | ggt | acc | cca | gct | gcg | aca | ttg | 432 |
| Thr | Ser | Phe | Val | Met | Trp | Phe | Gly | Glu | Gly | Thr | Pro | Ala | Ala | Thr | Leu | |
| | 130 | | | | | 135 | | | | | 140 | | | | | |
| aag | tgt | ggt | gcc | tac | act | atc | gtc | tat | gca | cct | ata | aaa | gac | caa | aca | 480 |
| Lys | Cys | Gly | Ala | Tyr | Thr | Ile | Val | Tyr | Ala | Pro | Ile | Lys | Asp | Gln | Thr | |
| 145 | | | | | 150 | | | | | 155 | | | | | 160 | |
| gat | ccc | gca | cca | aga | tat | atc | tct | ggt | gaa | gtt | aca | tct | gta | acc | ttt | 528 |
| Asp | Pro | Ala | Pro | Arg | Tyr | Ile | Ser | Gly | Glu | Val | Thr | Ser | Val | Thr | Phe | |
| | | | | 165 | | | | | 170 | | | | | 175 | | |
| gaa | aag | agt | gat | aat | aca | gtt | aaa | atc | aag | gtt | aac | ggt | cag | gat | ttc | 576 |
| Glu | Lys | Ser | Asp | Asn | Thr | Val | Lys | Ile | Lys | Val | Asn | Gly | Gln | Asp | Phe | |
| | | | 180 | | | | | 185 | | | | | 190 | | | |
| agc | act | ctc | tct | gct | aat | tca | agt | agt | cca | act | gaa | aat | ggc | gga | tct | 624 |
| Ser | Thr | Leu | Ser | Ala | Asn | Ser | Ser | Ser | Pro | Thr | Glu | Asn | Gly | Gly | Ser | |
| | | 195 | | | | | 200 | | | | | 205 | | | | |
| gcg | ggt | cag | gct | tca | tca | aga | tca | aga | aga | tca | ctc | tca | gag | gaa | acc | 672 |
| Ala | Gly | Gln | Ala | Ser | Ser | Arg | Ser | Arg | Arg | Ser | Leu | Ser | Glu | Glu | Thr | |
| | 210 | | | | | 215 | | | | | 220 | | | | | |
| agt | gaa | gct | gct | gca | acc | gtc | gat | ttg | ttt | gcc | ttt | acc | ctt | gat | ggt | 720 |
| Ser | Glu | Ala | Ala | Ala | Thr | Val | Asp | Leu | Phe | Ala | Phe | Thr | Leu | Asp | Gly | |
| 225 | | | | | 230 | | | | | 235 | | | | | 240 | |
| ggt | aaa | aga | att | gaa | gtg | gct | gta | cca | aac | gtc | gaa | gat | gca | tct | aaa | 768 |
| Gly | Lys | Arg | Ile | Glu | Val | Ala | Val | Pro | Asn | Val | Glu | Asp | Ala | Ser | Lys | |
| | | | | 245 | | | | | 250 | | | | | 255 | | |
| aga | gac | aag | tac | agt | ttg | gtt | gca | gac | gat | aaa | cct | ttc | tat | acc | ggc | 816 |
| Arg | Asp | Lys | Tyr | Ser | Leu | Val | Ala | Asp | Asp | Lys | Pro | Phe | Tyr | Thr | Gly | |
| | | | 260 | | | | | 265 | | | | | 270 | | | |
| gca | aac | agc | ggc | act | acc | aat | ggt | gtc | tac | agg | ttg | aat | gag | aac | gga | 864 |
| Ala | Asn | Ser | Gly | Thr | Thr | Asn | Gly | Val | Tyr | Arg | Leu | Asn | Glu | Asn | Gly | |
| | | 275 | | | | | 280 | | | | | 285 | | | | |
| gac | ttg | gtt | gat | aag | gac | aac | aca | gtt | ctt | ttg | aag | gat | gct | ggt | tcc | 912 |

```
Asp Leu Val Asp Lys Asp Asn Thr Val Leu Leu Lys Asp Ala Gly Ser
    290                 295                 300 tct gct ttt gga ctc aga tac atc gtt cct tcc gtt ttt gca atc ttt      960
Ser Ala Phe Gly Leu Arg Tyr Ile Val Pro Ser Val Phe Ala Ile Phe
305                 310                 315                 320 gca gcc tta ttc gtg ttg taa                                          981
Ala Ala Leu Phe Val Leu
                325

<210> SEQ ID NO 2
<211> LENGTH: 222
<212> TYPE: PRT
<213> ORGANISM: Cryptosporidium parvum

<400> SEQUENCE: 2

Met Arg Leu Ser Leu Ile Ile Val Leu Leu Ser Val Ile Val Ser Ala
1               5                   10                  15

Val Phe Ser Ala Pro Ala Val Pro Leu Arg Gly Thr Leu Lys Asp Val
            20                  25                  30

Pro Val Glu Gly Ser Ser Ser Ser Ser Ser Ser Ser Ser Ser Ser Ser
        35                  40                  45

Ser Ser Ser Ser Ser Ser Thr Ser Thr Val Ala Pro Ala Asn Lys
    50                  55                  60

Ala Arg Thr Gly Glu Asp Ala Glu Gly Ser Gln Asp Ser Ser Gly Thr
65                  70                  75                  80

Glu Ala Ser Gly Ser Gln Gly Ser Glu Glu Gly Ser Glu Asp Asp
                85                  90                  95

Gly Gln Thr Ser Ala Ala Ser Gln Pro Thr Thr Pro Ala Gln Ser Glu
            100                 105                 110

Gly Ala Thr Thr Glu Thr Ile Glu Ala Thr Pro Lys Glu Glu Cys Gly
        115                 120                 125

Thr Ser Phe Val Met Trp Phe Gly Glu Gly Thr Pro Ala Ala Thr Leu
    130                 135                 140

Lys Cys Gly Ala Tyr Thr Ile Val Tyr Ala Pro Ile Lys Asp Gln Thr
145                 150                 155                 160

Asp Pro Ala Pro Arg Tyr Ile Ser Gly Glu Val Thr Ser Val Thr Phe
                165                 170                 175

Glu Lys Ser Asp Asn Thr Val Lys Ile Lys Val Asn Gly Gln Asp Phe
            180                 185                 190

Ser Thr Leu Ser Ala Asn Ser Ser Pro Thr Glu Asn Gly Gly Ser
        195                 200                 205

Ala Gly Gln Ala Ser Ser Arg Ser Arg Arg Ser Leu Ser Glu
    210                 215                 220

<210> SEQ ID NO 3
<211> LENGTH: 666
<212> TYPE: DNA
<213> ORGANISM: Cryptosporidium parvum
<220> FEATURE:
<221> NAME/KEY: CDS
<222> LOCATION: (1)...(666)

<400> SEQUENCE: 3 atg aga ttg tcg ctc att atc gta tta ctc tcc gtt ata gtc tcc gct      48
Met Arg Leu Ser Leu Ile Ile Val Leu Leu Ser Val Ile Val Ser Ala
1               5                   10                  15 gta ttc tca gcc cca gcc gtt cca ctc aga gga act tta aag gat gtt     96
Val Phe Ser Ala Pro Ala Val Pro Leu Arg Gly Thr Leu Lys Asp Val
            20                  25                  30
```

```
cct gtt gag ggc tca tca tcg tca tcg tca tca tca tca            144
Pro Val Glu Gly Ser Ser Ser Ser Ser Ser Ser Ser Ser
         35                  40                  45 tca tca tca tca tca tca aca tca acc gtc gca cca gca aat aag    192
Ser Ser Ser Ser Ser Ser Thr Ser Thr Val Ala Pro Ala Asn Lys
 50                  55                  60 gca aga act gga gaa gac gca gaa ggc agt caa gat tct agt ggt act  240
Ala Arg Thr Gly Glu Asp Ala Glu Gly Ser Gln Asp Ser Ser Gly Thr
 65                  70                  75                  80 gaa gct tct ggt agc cag ggt tct gaa gag gaa ggt agt gaa gac gat  288
Glu Ala Ser Gly Ser Gln Gly Ser Glu Glu Glu Gly Ser Glu Asp Asp
                 85                  90                  95 ggc caa act agt gct gct tcc caa ccc act act cca gct caa agt gaa  336
Gly Gln Thr Ser Ala Ala Ser Gln Pro Thr Thr Pro Ala Gln Ser Glu
             100                 105                 110 ggc gca act acc gaa acc ata gaa gct act cca aaa gaa gaa tgc ggc  384
Gly Ala Thr Thr Glu Thr Ile Glu Ala Thr Pro Lys Glu Glu Cys Gly
         115                 120                 125 act tca ttt gta atg tgg ttc gga gaa ggt acc cca gct gcg aca ttg  432
Thr Ser Phe Val Met Trp Phe Gly Glu Gly Thr Pro Ala Ala Thr Leu
     130                 135                 140 aag tgt ggt gcc tac act atc gtc tat gca cct ata aaa gac caa aca  480
Lys Cys Gly Ala Tyr Thr Ile Val Tyr Ala Pro Ile Lys Asp Gln Thr
145                 150                 155                 160 gat ccc gca cca aga tat atc tct ggt gaa gtt aca tct gta acc ttt  528
Asp Pro Ala Pro Arg Tyr Ile Ser Gly Glu Val Thr Ser Val Thr Phe
                165                 170                 175 gaa aag agt gat aat aca gtt aaa atc aag gtt aac ggt cag gat ttc  576
Glu Lys Ser Asp Asn Thr Val Lys Ile Lys Val Asn Gly Gln Asp Phe
            180                 185                 190 agc act ctc tct gct aat tca agt agt cca act gaa aat ggc gga tct  624
Ser Thr Leu Ser Ala Asn Ser Ser Ser Pro Thr Glu Asn Gly Gly Ser
        195                 200                 205 gcg ggt cag gct tca tca aga tca aga aga tca ctc tca gag          666
Ala Gly Gln Ala Ser Ser Arg Ser Arg Arg Ser Leu Ser Glu
    210                 215                 220

<210> SEQ ID NO 4
<211> LENGTH: 30
<212> TYPE: PRT
<213> ORGANISM: Cryptosporidium parvum

<400> SEQUENCE: 4

Met Arg Leu Ser Leu Ile Ile Val Leu Leu Ser Val Ile Val Ser Ala
 1               5                  10                  15

Val Phe Ser Ala Pro Ala Val Pro Leu Arg Gly Thr Leu Lys
             20                  25                  30

<210> SEQ ID NO 5
<211> LENGTH: 192
<212> TYPE: PRT
<213> ORGANISM: Cryptosporidium parvum

<400> SEQUENCE: 5

Asp Val Pro Val Glu Gly Ser Ser Ser Ser Ser Ser Ser Ser Ser Ser
 1               5                  10                  15

Ser Ser Ser Ser Ser Ser Ser Ser Thr Ser Thr Val Ala Pro Ala
             20                  25                  30

Asn Lys Ala Arg Thr Gly Glu Asp Ala Glu Gly Ser Gln Asp Ser Ser
         35                  40                  45
```

```
Gly Thr Glu Ala Ser Gly Ser Gln Gly Ser Glu Glu Gly Ser Glu
    50                  55                  60

Asp Asp Gly Gln Thr Ser Ala Ala Ser Gln Pro Thr Thr Pro Ala Gln
65                  70                  75                  80

Ser Glu Gly Ala Thr Thr Glu Thr Ile Glu Ala Thr Pro Lys Glu Glu
                    85                  90                  95

Cys Gly Thr Ser Phe Val Met Trp Phe Gly Glu Gly Thr Pro Ala Ala
                100                 105                 110

Thr Leu Lys Cys Gly Ala Tyr Thr Ile Val Tyr Ala Pro Ile Lys Asp
            115                 120                 125

Gln Thr Asp Pro Ala Pro Arg Tyr Ile Ser Gly Glu Val Thr Ser Val
    130                 135                 140

Thr Phe Glu Lys Ser Asp Asn Thr Val Lys Ile Lys Val Asn Gly Gln
145                 150                 155                 160

Asp Phe Ser Thr Leu Ser Ala Asn Ser Ser Pro Thr Glu Asn Gly
                165                 170                 175

Gly Ser Ala Gly Gln Ala Ser Ser Arg Ser Arg Arg Ser Leu Ser Glu
            180                 185                 190
```

<210> SEQ ID NO 6
<211> LENGTH: 326
<212> TYPE: PRT
<213> ORGANISM: Cryptosporidium parvum

<400> SEQUENCE: 6

```
Met Arg Leu Ser Leu Ile Ile Val Leu Leu Ser Val Ile Val Ser Ala
1               5                   10                  15

Val Phe Ser Ala Pro Ala Val Pro Leu Arg Gly Thr Leu Lys Asp Val
                20                  25                  30

Pro Val Glu Gly Ser Ser Ser Ser Ser Ser Ser Ser Ser Ser Ser Ser
            35                  40                  45

Ser Ser Ser Ser Ser Ser Ser Thr Ser Thr Val Ala Pro Ala Asn Lys
    50                  55                  60

Ala Arg Thr Gly Glu Asp Ala Glu Gly Ser Gln Asp Ser Ser Gly Thr
65                  70                  75                  80

Glu Ala Ser Gly Ser Gln Gly Ser Glu Glu Gly Ser Glu Asp Asp
                85                  90                  95

Gly Gln Thr Ser Ala Ala Ser Gln Pro Thr Thr Pro Ala Gln Ser Glu
                100                 105                 110

Gly Ala Thr Thr Glu Thr Ile Glu Ala Thr Pro Lys Glu Glu Cys Gly
            115                 120                 125

Thr Ser Phe Val Met Trp Phe Gly Glu Gly Thr Pro Ala Ala Thr Leu
    130                 135                 140

Lys Cys Gly Ala Tyr Thr Ile Val Tyr Ala Pro Ile Lys Asp Gln Thr
145                 150                 155                 160

Asp Pro Ala Pro Arg Tyr Ile Ser Gly Glu Val Thr Ser Val Thr Phe
                165                 170                 175

Glu Lys Ser Asp Asn Thr Val Lys Ile Lys Val Asn Gly Gln Asp Phe
                180                 185                 190

Ser Thr Leu Ser Ala Asn Ser Ser Pro Thr Glu Asn Gly Gly Ser
            195                 200                 205

Ala Gly Gln Ala Ser Ser Arg Ser Arg Arg Ser Leu Ser Glu Glu Thr
    210                 215                 220

Ser Glu Ala Ala Ala Thr Val Asp Leu Phe Ala Phe Thr Leu Asp Gly
```

```
                225                 230                 235                 240
Gly Lys Arg Ile Glu Val Ala Val Pro Asn Val Asp Ala Ser Lys
                    245                 250                 255
Arg Asp Lys Tyr Ser Leu Val Ala Asp Lys Pro Phe Tyr Thr Gly
            260                 265                 270
Ala Asn Ser Gly Thr Thr Asn Gly Val Tyr Arg Leu Asn Glu Asn Gly
        275                 280                 285
Asp Leu Val Asp Lys Asp Asn Thr Val Leu Leu Lys Asp Ala Gly Ser
    290                 295                 300
Ser Ala Phe Gly Leu Arg Tyr Ile Val Pro Ser Val Phe Ala Ile Phe
305                 310                 315                 320
Ala Ala Leu Phe Val Leu
            325

<210> SEQ ID NO 7
<211> LENGTH: 315
<212> TYPE: DNA
<213> ORGANISM: Cryptosporidium parvum
<220> FEATURE:
<221> NAME/KEY: CDS
<222> LOCATION: (1)...(312)

<400> SEQUENCE: 7 gaa acc agt gaa gct gct gca acc gtc gat ttg ttt gcc ttt acc ctt      48
Glu Thr Ser Glu Ala Ala Ala Thr Val Asp Leu Phe Ala Phe Thr Leu
  1               5                  10                  15 gat ggt ggt aaa aga att gaa gtg gct gta cca aac gtc gaa gat gca      96
Asp Gly Gly Lys Arg Ile Glu Val Ala Val Pro Asn Val Glu Asp Ala
             20                  25                  30 tct aaa aga gac aag tac agt ttg gtt gca gac gat aaa cct ttc tat     144
Ser Lys Arg Asp Lys Tyr Ser Leu Val Ala Asp Asp Lys Pro Phe Tyr
         35                  40                  45 acc ggc gca aac agc ggc act acc aat ggt gtc tac agg ttg aat gag     192
Thr Gly Ala Asn Ser Gly Thr Thr Asn Gly Val Tyr Arg Leu Asn Glu
     50                  55                  60 aac gga gac ttg gtt gat aag gac aac aca gtt ctt ttg aag gat gct     240
Asn Gly Asp Leu Val Asp Lys Asp Asn Thr Val Leu Leu Lys Asp Ala
 65                  70                  75                  80 ggt tcc tct gct ttt gga ctc aga tac atc gtt cct tcc gtt ttt gca     288
Gly Ser Ser Ala Phe Gly Leu Arg Tyr Ile Val Pro Ser Val Phe Ala
                 85                  90                  95 atc ttt gca gcc tta ttc gtg ttg taa                                 315
Ile Phe Ala Ala Leu Phe Val Leu
            100

<210> SEQ ID NO 8
<211> LENGTH: 104
<212> TYPE: PRT
<213> ORGANISM: Cryptosporidium parvum

<400> SEQUENCE: 8

Glu Thr Ser Glu Ala Ala Ala Thr Val Asp Leu Phe Ala Phe Thr Leu
  1               5                  10                  15

Asp Gly Gly Lys Arg Ile Glu Val Ala Val Pro Asn Val Glu Asp Ala
             20                  25                  30

Ser Lys Arg Asp Lys Tyr Ser Leu Val Ala Asp Asp Lys Pro Phe Tyr
         35                  40                  45

Thr Gly Ala Asn Ser Gly Thr Thr Asn Gly Val Tyr Arg Leu Asn Glu
     50                  55                  60
```

-continued

```
Asn Gly Asp Leu Val Asp Lys Asp Asn Thr Val Leu Leu Lys Asp Ala
 65                  70                  75                  80

Gly Ser Ser Ala Phe Gly Leu Arg Tyr Ile Val Pro Ser Val Phe Ala
                 85                  90                  95

Ile Phe Ala Ala Leu Phe Val Leu
            100
```

GP40 AND USES THEREOF

STATEMENT AS TO FEDERALLY SPONSORED RESEARCH

This work is funded in part by the National Institutes of Health under Grant Nos. AI33384, AI40344, DK34928P30 and AI07389. The government therefore may have certain rights to this invention.

BACKGROUND

*Cryptosporidium parvum* (*C. parvum*), an intestinal Apicomplexan parasite, is a significant cause of diarrheal disease worldwide (Griffiths, 1998. *Adv Parasitol.* 40:37–85). In immunocompetent individuals, the disease is usually self-limiting, but it can be chronic and life threatening in immunocompromised patients such as those with AIDS.

*C. parvum* has also been associated with diarrheal disease in children in daycare centers, travelers, animal handlers and hospital personnel. Recently, the parasite has gained notoriety as the causative agent of numerous outbreaks of waterborne diarrheal disease. There is currently no effective, specific therapy approved for disease caused by this parasite.

*C. parvum* infection is initiated by ingestion of oocysts which, upon exposure to favorable conditions within the host, undergo excystation. Released sporozoites attach to and invade host cells forming a parasitophorus vacuole where the parasite undergoes further intracellular development through asexual and sexual cycles eventually leading to formation of new oocysts that are capable of reinitiating the infectious cycle. The ultrastructural aspects of the processes of attachment and invasion and various factors influencing attachment have been characterized (Tzipori et al., 1998. *Adv Parasitol.* 40:5–36; Hamer etal., 1994. *Infect Immun.* 62:2208–2213). However, the molecular basis of these host-parasite interactions is not well understood (Ward et al., 1998. *Adv Parasitol.* 40:151–185).

SUMMARY

The present invention is based, in part, on the discovery of a gene, gp40gp 15 (SEQ ID NO:1). The gp40gp15 cDNA described below is a 981 nucleotide sequence which encodes a 49 KDa precursor protein (SEQ ID NO:6) of *C. parvum*. The precursor protein is proteolytically cleaved to yield two glycoproteins, gp40 (SEQ ID NO:2) and gp15 (SEQ ID NO:8). gp40 protein is a 40 KDa glycoprotein which is present in oocysts and sporozoites and is also shed from the parasite during invasion. gp40 protein mediates sporozoite attachment and invasion of host cells and is therefore useful as a target for prevention or therapy of cryptosporidiosis.

Accordingly, in one aspect, the invention features an isolated nucleic acid molecule comprising a nucleotide sequence encoding a gp40 protein or a biologically active portion thereof, as well as nucleic acid fragments suitable as primers or hybridization probes for the detection of a gp40-encoding nucleic acid (e.g., gp40 mRNA). The gp40 nucleotide sequence, nucleotides 1–666 of SEQ ID NO:1; SEQ ID NO:3, encodes a 222 amino acid protein (SEQ ID NO:2). gp40 protein includes a signal sequence of around 30 amino acids (from amino acid 1 to amino acid 30 of SEQ ID NO:2; SEQ ID NO:4) and has a mature protein length of 192 amino acids (amino acids 31–222 of SEQ ID NO:2; SEQ ID NO:5). gp40 protein possesses a polyserine domain (at amino acids 37 to 55 of SEQ ID NO:2) with multiple predicted O-glycosylation sites. The protein also has a hydrophobic stretch of amino acids in its C-terminal region consistent with that required for GPI-anchoring.

In one embodiment, an isolated gp40 nucleic acid molecule includes the nucleotide sequence of SEQ ID NO:3, or a complement of these nucleotide sequences. In another embodiment, the isolated nucleic acid molecule of the invention includes a nucleotide sequence which hybridizes, preferably under stringent conditions, to or has at least about 60–65%, preferably at least about 70–75%, more preferably at least about 80–85%, and even more preferably at least about 90–95%, 96%, 97%, 98% or 99% sequence identity to the nucleotide sequence shown in SEQ ID NO:3, or a portion thereof. In yet another embodiment, the isolated nucleic acid molecule encodes the amino acid sequence of SEQ ID NO:2 or SEQ ID NO:5. gp40 nucleic acid molecules can encode a protein which possesses at least one of the gp40 activities described herein, e.g., the ability to bind human intestinal epithelial cells.

In another embodiment, the isolated nucleic acid molecule encodes a protein or portion thereof wherein the protein or portion thereof includes an amino acid sequence which is sufficiently homologous to the amino acid sequence of SEQ ID NO:2 or SEQ ID NO:5 such that the protein or portion thereof possesses a gp40 biological activity, e.g., the ability to bind intestinal epithelial cells. The protein or portion thereof encoded by the nucleic acid molecule maintains the ability to play a role in mediating the attachment and invasion of host cells by *C. parvum*. In yet another embodiment, the protein encoded by the nucleic acid molecule has at least about 60–70%, preferably at least about 80–85%, and more preferably at least about 86%, 88%, 90%, and most preferably at least about 90–95%, 96%, 97%, 98% or 99% sequence identity to the amino acid sequence of SEQ ID NO:2 or SEQ ID NO:5. In one embodiment, the protein is a full length protein which is substantially homologous to the entire amino acid sequence of SEQ ID NO:2.

In another embodiment, the isolated nucleic acid molecule encodes a portion of a gp40 protein, e.g., a portion which includes a sequence encoding a polyserine domain with multiple O-glycosylation sites.

In another embodiment, the isolated nucleic acid molecule encodes a gp40 protein, or portion thereof, which has at least about 55%, 65%, 75%, 85% or 95% identity to SEQ ID NO:2 or SEQ ID NO:5, and has one or more of the following activities:1) it is involved in parasite-host interactions; 2) it interacts, directly or indirectly, with a host cell, e.g., a human intestinal epithelial cell; or 3) it modulates the ability of *C. parvum* sporozoites to attach and invade a host cell.

In another embodiment, the isolated nucleic acid molecule is at least 15 (30, 50, 100, 200, 300, 400, 500, 600, 700, 800, or 900) nucleotides in length and hybridizes under stringent conditions to a nucleic acid molecule consisting of the nucleotide sequence of SEQ ID NO:3.

Given the disclosure herein of gp40-encoding sequence (e.g., SEQ ID NO:3), antisense nucleic acid molecules (i.e., molecules which are complementary to the gp40 nucleotide sequence) are also provided by the invention.

In another embodiment, the encoded gp40 protein differs in amino acid sequence at least 1 to as many as 2, 3, 5, 10, 20 or 40 residues from a sequence in SEQ ID NO:2 or SEQ ID NO:5. In one embodiment, the differences are such that the gp40 encoded protein exhibits a gp40 biological activity, e.g., the encoded gp40 protein retains a biological activity of a naturally-occurring gp40, e.g., the gp40 protein of SEQ ID NO:2 or SEQ ID NO:5.

In another embodiment the encoded gp40 protein includes a gp40 sequence described herein as well as other N-terminal and/or C-terminal amino acid sequence.

The invention also features vectors, e.g., recombinant expression vectors, containing the nucleic acid molecules of the invention and host cells into which such vectors have been introduced. In one embodiment, such a host cell is used to produce gp40 protein by culturing the host cell in a suitable medium. The gp40 protein can be then isolated from the medium or the host cell.

In yet another embodiment, the biologically active portion of the gp40 protein includes a domain or motif, preferably a domain or motif which has a gp40 activity. The motif can be e.g., a short hydrophobic region at the C-terminus, consistent with that required for addition of a GPI anchor; a polyserine domain which has multiple predicted O-glycosylation sites which may be used by the parasite to bind a host cell; a carbohydrate domain; or a N-glycosylation site.

The invention also provides an isolated preparation of a gp40 protein. In one embodiment, the gp40 protein includes the amino acid sequence of SEQ ID NO:2 or SEQ ID NO:5. In another embodiment, the invention pertains to an isolated full length protein which is substantially homologous to the entire amino acid sequence of SEQ ID NO:2 (encoded by SEQ ID NO:3) or the mature amino acid sequence of SEQ ID NO:5. In yet another embodiment, the protein has at least about 60–70%, preferably at least about 80–85%, and more preferably at least about 86%, 88%, 90%, and most preferably at least about 90–95%, 96%, 97%, 98% or 99% sequence identity to the entire amino acid sequence of SEQ ID NO:2 or SEQ ID NO:5. In other embodiments, the isolated gp40 protein includes an amino acid sequence which has at least about 60–70% or more sequence identity to the amino acid sequence of SEQ ID NO:2 or SEQ ID NO:5 and has an one or more of the following activities: 1) it is involved in parasite-host interactions: 2) it interacts, directly or indirectly, with a host cell, e.g., a human intestinal epithelial cell; or 3) it modulates the ability of *C. parvum* sporozoites to attach and invade a host cell.

In yet another embodiment, the gp40 protein differs in amino acid sequence at up to 1, 2, 3, 5, or 10% of the residues from a sequence in SEQ ID NO:2 or SEQ ID NO:5. The differences are such that: the gp40 protein exhibits a gp40 biological activity, e.g., the gp40 protein retains a biological activity of a naturally occurring gp40.

In another aspect of the invention, the gp40 protein is a recombinant gp40 protein which differs from gp40 isolated from oocysts of *C. parvum* in its pattern of glycosylation or other posttranslational modifications.

The gp40 protein, portions or fragments thereof, can be used to prepare anti-gp40 antibodies. Accordingly, the invention also provides an antigenic peptide of gp40 which includes at least 8, 10, 20, 30, 50, 70 or 80 amino acid residues of the amino acid sequence shown in SEQ ID NO:2 or SEQ ID NO:5, and encompasses an epitope of gp40 such that an antibody raised against the peptide forms a specific immune complex with gp40. The invention further provides an antibody, e.g., a monoclonal antibody such as 4E9, or a monoclonal antibody that specifically binds gp40. In another embodiment, the antibody is coupled to a detectable substance. In yet another embodiment, the antibody is incorporated into a pharmaceutical composition comprising the antibody and a pharmaceutically acceptable carrier.

In another aspect, the invention features a method of inhibiting attachment and/or infection of a host by *C. parvum* by administering to an animal a therapeutically effective amount of a compound which inhibits gp40 expression or activity. The animal can be any mammal, including a human, a monkey, a horse, a pig, a cow or a sheep. The compound can be any molecule that binds to gp40, or to a gp40 target binding molecule, and inhibits the ability of *C. parvum* to attach and/or infect a host cell, e.g., an epithelial cell. The compound can be a polypeptide selected for binding in, e.g., a phage display or two-hybrid assay; an antibody that is specifically reactive with gp40 or gp40 binding protein; a gp40 antisense molecule; fusions of gp40; a small molecule, e.g., a small molecule which binds to the control region of gp40; or an agent. A compound which modulates gp40 activity can be a compound which decreases gp40 protein activity or gp40 nucleic acid expression. In another embodiment, the method includes administering a nucleic acid which encodes one of the above-described compounds.

In another aspect, the invention features, a method of modulating a gp40 activity, in vitro or in vivo. The method includes contacting gp40 with a compound that modulates the activity of gp40. gp40 activity may be modulated by administering: a gp40 antisense molecule; an antibody; a gp40 target binding protein (i.e., a protein that binds GP40), or a gp40 target binding portion thereof, e.g., a polypeptide selected for binding in, e.g., a phage display or two hybrid assay; a small molecule, e.g., a small molecule which binds to the control region of gp40. In another embodiment, the method includes administering a nucleic acid which encodes one of the above-described agents. A biological activity of gp40 that can modulated by the present method includes: 1) modulating an interaction, directly or indirectly, with a gp40 target binding protein, e.g., a gp40 target binding protein on a human intestinal epithelial cell; or 2) inhibiting the attachment of sporozoites of *C. parvum* to intestinal epithelial cells. In another embodiment, gp40 is a *C. parvum* sporozoite present within a subject and the agent is administered to the subject.

The invention also features methods for evaluating a subject suspected of having a *C. parvum* infection. The method includes evaluating, e.g., detecting, the presence of a gp40 gene or gp40 protein in a sample, thereby determining if a subject is infected with *C. parvum*. In one embodiment, the method includes evaluating, e.g., in a sample of cells from the subject, the presence or absence of gp40, e.g., by contacting the sample with a nucleic acid probe capable of hybridizing to gp40 mRNA, e.g., a labeled probe or contacting a sample with an antibody capable of binding to gp40 protein, e.g., a labeled antibody; or by detecting the presence of *C. parvum* by using an ELISA that contains an antibody which specifically binds to gp40 and evaluates the level of *C. parvum* gp40 in the sera. A patient may be evaluated for the presence of antibodies directed against gp40 by obtaining a biological sample form the patient, e.g., a serum sample, contacting the sample with gp40 protein (or a fragment thereof) and determining if there are antibodies which bind the gp40 protein present in the biological sample.

The invention also features methods for identifying a compound or agent which interacts with a gp40 protein. In one embodiment, the interaction with a gp40 protein can be binding, phosphorylation, or otherwise interacting to form or break a bond, e.g., a covalent or non-covalent bond. A compound can include, for example, a fragment or analog of a gp40 binding polypeptide, e.g., a randomly generated polypeptide which interacts with gp40, or a small molecule. In another embodiment, the method can include the steps of contacting the gp40 protein with the compound or agent under conditions which allow binding of the compound to the gp40 protein to form a complex and detecting the formation of a complex of the gp40 protein and the compound in which the ability of the compound to bind to the gp40 protein is indicated by the presence of the compound in the complex. Methods for identifying a compound or agent can be performed, for example, using a cell free assay or a cell-based assay.

In another aspect, the invention features methods for identifying compounds which modulate gp40 nucleic acid expression. In one embodiment, nucleic acid expression can be evaluated using a nucleic acid probe, e.g., a labeled probe, capable of hybridizing to a gp40 nucleic acid molecule, e.g., gp40 mRNA. gp40 expression can be evaluated, for example, by detecting the production of gp40 protein, e.g., using an antibody, e.g., a labeled antibody, or by determining a cell activity, e.g., using a marker gene, e.g., a lacZ gene, fused to the control region of gp40 and following production of the marker.

A "purified" or "substantially pure" or "isolated" polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 µg of the polypeptide; at least 1, 10, or 100 mg of the polypeptide.

An "isolated" or "pure nucleic acid", e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA can also include a recombinant DNA which is part of a hybrid gene encoding sequence. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The terms "peptides", "proteins", and "polypeptides" are used interchangeably herein.

A "biological activity of gp40" refers to one or more of the following activities: 1) it is involved in parasite-lost interactions: 2) it interacts, directly or indirectly, with a host cell, e.g., a human intestinal epithelial cell; or 3) it modulates the ability of C. parvum sporozoites to attach and invade a host cell.

The term "small molecule", as used herein, includes peptides, peptidomimetics, or non-peptidic compounds, such as organic molecules, having a molecular weight less than 2000, preferably less than 1000.

Other features and advantages of the invention will be apparent from the following detailed description, and from the claims.

DESCRIPTION OF DRAWINGS

FIG. 1 depicts the nucleic acid sequence of gp40gp 15 (SEQ ID NO:1).

FIG. 2 depicts the nucleic acid sequence of gp40 (SEQ ID NO:3).

FIG. 3 depicts the predicted amino acid sequence of gp40 (SEQ ID NO:2).

FIG. 4 depicts the nucleic acid sequence of gp15 (SEQ ID NO:7).

FIG. 5 depicts the predicted amino acid sequence of gp15 (SEQ ID NO:8).

FIG. 6 depicts the predicted amino acid sequence of gp49 precursor protein (SEQ ID NO:6).

DETAILED DESCRIPTION

Figure 7B:
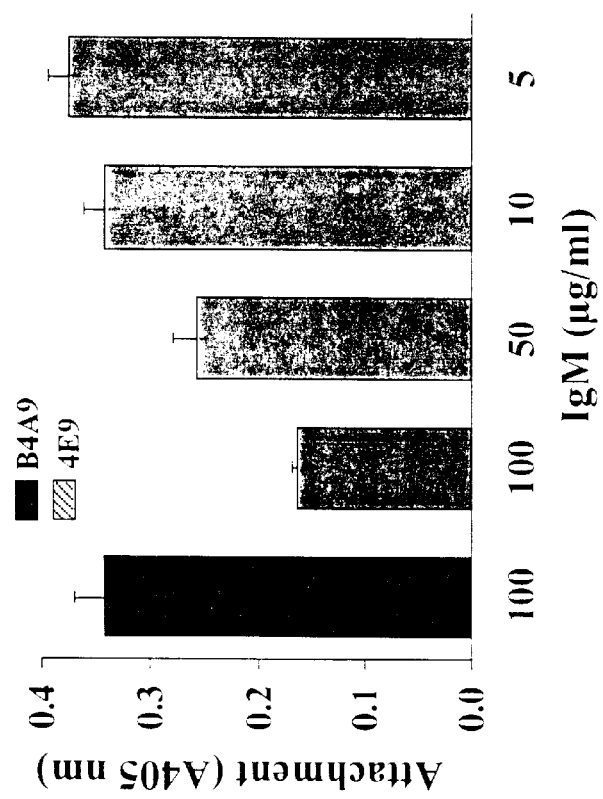
FIGS. 7A–B are histograms depicting the effect of MAb 4E9 on C. parvum infection or attachment to CACO-2A cells, respectively. Results are expressed as a percentage of the control.

The present invention is based on the discovery of a gene, gp 15gp40 (SEQ ID NO:1), which encodes a precursor glycoprotein (SEQ ID NO:6). The precursor glycoprotein is proteolytically degraded yielding two novel glycoproteins of C. parvum. The glycoproteins, referred to herein as gp40 (SEQ ID NO:2) and gp15 (SEQ ID NO:8), play a role in C. parvum pathogenesis. gp40 protein is a 40 KDa glycoprotein which is present in oocysts and sporozoites and is also shed from the parasite during invasion. The nucleotide and amino acid sequence of gp40 are shown in FIG. 2 (SEQ ID NO:3) and FIG. 3 (SEQ ID NO:2), respectively.

gp40 was first identified using monoclonal antibody (MAb) 4E9 which was raised against sporozoite surface proteins of C. parvum. Characterization of gp40 revealed that it is a 40 kDa glycoprotein which is present in C. parvum oocysts and sporozoites. The protein is also shed from the parasite during invasion of the host cell. Carbohydrate analysis of gp40 revealed that gp40 contains terminal α-linked GalNAc residues which are most likely O-glycosylated to Ser/Thr residues of the protein backbone.

gp40 is involved in mediating parasite-host interactions. This novel protein mediates interactions of C. parvum invasive stages (sporozoites and merozoites) with host intestinal cells. Antibodies reactive with gp40 block invasion and intracellular development of sporozoites. This effect is mediated in part by inhibition of sporozoite attachment to host cells. The α-GalNAc-containing O-linked oligosaccharides present on the surface of gp40 contribute to mediating adherence of C. parvum to host cells.

The involvement of gp40 C. parvum surface/apical complex proteins in the initial host-parasite interaction provides a basis for devising strategies for inhibiting this interaction. Thus, gp40 can serve as a target of potential specific preventive or therapeutic modalities. For example, gp40 can be used to treat cryptosporidiosis. In particular, gp40 can be used to treat cryptosporidiosis in AIDS patients. gp40 antagonists or inhibiting molecules are agents that inhibits gp40 gene expression or the activity of gp40 and can be administered therapeutically. Examples of gp40 antagonists include a gp40 antisense molecule, a gp40 antibody, a monomeric organic molecule, and a gp40 polypeptide that binds to gp40 target binding sites on host cells, thereby acting as competitive inhibitor of gp40 expressed on the surface of C. parvum.

C. parvum belongs to the phylum Apicomplexa and is a coccidian protozoan capable of parasitizing the intestinal tract of a variety of mammalian species. As discussed above, gp40 is critical for mediating the attachment and invasion of C. parvum with a host cell. It is predicted that gp40 is also likely to be critical for mediating the attachment and invasion of other pathogenic microbes, particularly protozoa, and even more particularly apicomplexans such as Eimeria and Plasmodium, with their host cell. Thus, the scope of the present invention encompasses methods of inhibiting and treating any microbial infection which depends on gp40 for pathogenesis.

gp40 Nucleic Acid Molecules

The invention pertains to isolated nucleic acid molecules that encode gp40 proteins or biologically active portions thereof, as well as nucleic acid molecules sufficient for use as hybridization probes to identify gp40 encoding nucleic acids (e.g., gp40 mRNA) and fragments for use as PCR primers for the amplification or mutation of gp40 nucleic acid molecules.

A nucleic acid molecule of the present invention, e.g., a nucleic acid molecule having the nucleotide sequence of SEQ ID NO:3, or a complement thereof, can be isolated using standard molecular biology techniques using the sequence information provided herein. Using all or portion of the nucleic acid sequences of SEQ ID NO:3 as a hybridization probe, gp40 nucleic acid molecules can be isolated using standard hybridization and cloning techniques (e.g., as described in Sambrook et al., eds.(1989, *Molecular Cloning: A Laboratory Manual. 2nd, ed., Cold Spring Harbor Laboratory*, Cold Spring Harbor Laboratory Press, Cold Spring Harbor, N.Y.).

The nucleic acid molecule of the invention can comprise only a portion of a nucleic acid sequence encoding gp40, for example, a fragment which can be used as a probe or primer, or a fragment encoding a biologically active portion of gp40. The nucleotide sequence determined from the cloning of the C. parvum gp40 gene allows for the generation of probes and primers designed for use in identifying and/or cloning gp40 homologues in other organisms, e.g., other microbes. The probe/primer typically comprises substantially purified oligonucleotide. The oligonucleotide typically comprises a region of nucleotide sequence that hybridizes under stringent conditions to at least about 12, preferably about 25, more preferably about 50, 100, 150, 200, 250, 300, 350 or 400 consecutive nucleotides of the sense or anti-sense sequence of SEQ ID NO:3, or of a naturally-occurring mutant of SEQ ID NO:3.

The invention further encompasses nucleic acid molecules that differ from the nucleotide sequence of SEQ ID NO:3 due to degeneracy of the genetic code and thus encode the same gp40 proteins as those encoded by the nucleotide sequences shown in SEQ ID NO:3. Moreover, nucleic acid molecules encoding gp40 proteins from other microbes (e.g., gp40 homologues), which have a nucleotide sequence which differs from that of a C. parvum gp40, are intended to be within the scope of the invention. Nucleic acid molecules corresponding to homologues of the gp40 nucleotide sequence of the invention can be isolated based on their identity to the C. parvum gp40 nucleic acids disclosed herein using the C. parvum cDNAs, or a portion thereof, as a hybridization probe according to standard hybridization techniques under stringent hybridization conditions.

Accordingly, in another embodiment, an isolated nucleic acid molecule of the invention is at least 15 (30, 50, 100, 250, or 500) nucleotides in length and hybridizes under stringent conditions to the nucleic acid molecule comprising the nucleotide sequence of SEQ ID NO:3.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. Typically, hybridization conditions initially used to identify related sequences are of low to moderate stringency. After hybridization, the nucleic acids are washed to dissociate duplexes that are bound together by some non-specific interaction. The stringency used in washing is typically higher than that used in hybridization. In general, it is desirable to increase the washing stringency when the degree of homology between the target nucleic acid and the probe sequence is expected to be high. Stringency-affecting parameters include, primarily, temperature and salt concentration. In general, the lower the salt concentration and the higher the temperature, the higher the stringency. Washing can be initiated at a low temperature (e.g., room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

An example of a progression from lower to higher stringency conditions is the following, where the salt content is given as the concentration of a sodium citrate/sodium chloride solution ("SSC"; for salt content of 20×SSC, see Sambrook et al., 1989, *Molecular Cloning, A Laboratory Manual*, 2nd Ed. Cold Spring Harbor Laboratory Press, Cold Spring Harbor, NY). Nucleic acid molecules are hybridized at 42° C. in 2×SSC/0.1% sodium dodecylsulfate ("SDS") and then washed in 0.2×SSC/0.1% SDS at room temperature (for conditions of low stringency); in 0.2×SSC/0.1% SDS at 42° C. (for conditions of moderate stringency); and in 0.1×SSC at 68° C. (for conditions of high stringency). Washing can be carried out using only one of the conditions given, or each of the conditions can be used for, e.g., 10–15 minutes each in the order listed above. Any or all of the washes can be repeated.

Preferably, an isolated nucleic acid molecule of the invention that hybridizes under stringent conditions to the sequence of SEQ ID NO:3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein and is present in, e.g., C. parvum).

Mutations which change the nucleotide sequence of SEQ ID NO:3, can lead to changes in the amino acid sequence of the encoded gp40 protein, without altering the functional ability of the gp40 protein are also within the scope of the invention. For example, one can make nucleotide substitutions leading to amino acid substitutions at "non-essential" amino acid residues. A "non-essential" amino acid residue is a residue that can be altered from the wild-type sequence of gp40 (e.g., the sequence of SEQ ID NO:2 or SEQ ID NO:5) without altering the biological activity, whereas an "essential" amino acid residue is required for biological activity. For example, amino acid residues that are conserved among the gp40 proteins of various microbes are predicted to be particularly unamenable to alteration. Thus, the invention pertains to nucleic acid molecules encoding gp40 proteins that contain changes in amino acid residues that are not essential for activity. Such gp40 proteins differ in amino acid sequence from SEQ ID NO:2 or SEQ ID NO:5, yet retain biological activity. In one embodiment, the isolated nucleic acid molecule includes a nucleotide sequence encoding a protein that includes an amino acid sequence that is at least about 60–70% identical, preferably at least about 70–75%, more preferably at least about 80–85%, and even more preferably at least about 90–95%, 96%, 97%, 98% or 99% identical to the amino acid sequence of SEQ ID NO:2 or SEQ ID NO:5.

An isolated nucleic acid molecule encoding a gp40 protein having a sequence which differs from that of SEQ ID NO:2 or SEQ ID NO:5, respectively, can be created by introducing one or more nucleotide substitutions, additions or deletions into the nucleotide sequence of SEQ ID NO:3 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysinc, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in gp40 is preferably replaced with another amino acid residue from the same side chain family. Alternatively, mutations can be introduced randomly along all or part of a gp40 coding sequence, such as by saturation mutagenesis, and the resultant mutants can be screened for gp40 biological activity to identify mutants that retain activity. Following mutagenesis, the encoded protein can be expressed recombinantly and the activity of the protein can be determined.

gp40 Proteins

The invention features isolated gp40 proteins, and biologically active portions thereof, as well as polypeptide fragments suitable for use as immunogens to raise anti-gp40 antibodies. In one embodiment, native gp40 proteins can be isolated from cells or tissue sources by an appropriate purification scheme using standard protein purification techniques. In another embodiment, gp40 proteins are produced by recombinant DNA techniques. Alternative to recombinant expression, a gp40 protein or polypeptide can be synthesized chemically using standard peptide synthesis techniques.

Biologically active portions of a gp40 protein include peptides comprising amino acid sequences sufficiently identical to or derived from the amino acid sequence of the gp40 protein (e.g., the amino acid sequence shown in SEQ ID NO:2 or SEQ ID NO:5), which include less amino acids than the full length gp40 proteins, and exhibit at least one activity of a gp40 protein. Typically, biologically active portions comprise a domain or motif with at least one activity of the gp40 protein. A biologically active portion of a gp40 protein can be a polypeptide which is, for example, 10, 25, 50, 100 or more amino acids in length. Preferred biologically active polypeptides include one or more identified gp40 structural domains, e.g., polyserine domain or a carbohydrate domain.

The comparison of sequences and determination of percent homology between two sequences can be accomplished using a mathematical algorithm. A preferred, non-limiting example of a mathematical algorithm utilized for the comparison of sequences is the algorithm of Karlin and Altschul *Proc. Natl. Acad. Sci. USA* 87:2264–68, 1990, modified as in Karlin and Altschul *Proc. Natl. Acad. Sci. USA* 90:5873–77, 1993. Such an algorithm is incorporated into the NBLAST and XBLAST programs (version 2.0) of Altschul, et al. *J. Mol. Biol.* 215:403–10, 1990. BLAST nucleotide searches can be performed with the NBLAST program, score=100, wordlength=12 to obtain nucleotide sequences homologous to gp40 nucleic acid molecules of the invention. BLAST protein searches can be performed with the XBLAST program, score=50, wordlength=3 to obtain amino acid sequences homologous to gp40 protein molecules of the invention. To obtain gapped alignments for comparison purposes. Gapped BLAST can be utilized as described in Altschul et al. (1997, *Nucleic Acids Res.* 25(17) :3389–3402). When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated in the ALIGN program (version 2.0) which is part of the GCG sequence alignment software package. When utilizing the ALIGN program for comparing amino acid sequences, a PAM120 weight residue table, a clap length penalty of 12, and a gap penalty of 4 can be used.

gp40 Chimeric or Fusion Proteins

The invention also provides gp40 chimeric or fusion proteins. As used herein, a gp40 "chimeric protein" or "fusion protein" comprises a gp40 polypeptide operatively linked to a non-gp40 polypeptide, e.g., by a peptide bond. A "gp40 polypeptide" refers to a polypeptide having an amino acid sequence corresponding to gp40, whereas a "non-gp40 polypeptide" refers to a polypeptide having an amino acid sequence corresponding to a protein which is not substantially identical to the gp40 protein, e.g., a protein which is different from the gp40 protein and which is derived from the same or a different organism. Within a gp40 fusion protein the gp40 polypeptide can correspond to all or a portion of a gp40 protein, preferably at least one biologically active portion of a gp40 protein. Within the fusion protein, the term "operatively linked" is intended to indicate that the gp40 polypeptide and the non-gp40 or polypeptide are fused in-frame to each other. The non-gp40 polypeptide can be fused to the N-terminus or C-terminus of the gp40 polypeptide. For example, one useful fusion protein is a GST-gp40 fusion protein in which the gp40 sequences are fused to the C-terminus of the GST sequences. Such fusion proteins can facilitate the purification of recombinant gp40.

Generation of gp40 Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate nucleic acids which encode an array of fragments. Nucleic acids which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences by Random Methods

Amino acid sequence variants of a protein can be prepared by random mutagenesis of DNA which encodes a protein or a particular domain or region of a protein. Useful methods include PCR mutagenesis (Leung et al, 1989, *Technique* 1:11–15) and saturation mutagenesis (Mayers et al., 1985, *Science* 229:242). A library of random amino acid sequence variants can also be generated by the synthesis of a set of degenerate oligonucleotide sequences (Narang, SA (1983) *Tetrahedron* 39:3; Itakura et al. (1984) *Annu. Rev. Biochem.* 53:323). Non-random or directed, mutagenesis techniques can be used to provide specific sequences or mutations in specific regions. These techniques can be used to create variants which include, e.g., deletions, insertions, or substitutions, of residues of the known amino acid sequence of a protein. For example, alanine scanning mutagenesis is a useful method for identification of certain residues or regions of the desired protein that are preferred locations or domains for mutagenesis, Cunningham and Wells (*Science* 244:1081–1085, 1989). Oligonucleotide-mediated mutagenesis is also a useful method for preparing substitution, deletion, and insertion variants of DNA (Adelman et al., (*DNA* 2:183, 1983). Another method for preparing variants is cassette mutagenesis which is based on the technique described by Wells et al. (*Gene*, 34:315, 1985).

Expression Control Sequences and Vectors

Various uses of the gp40 nucleic acids will involve cloning of gp40 sequences into a vector, where they are operably linked to one or more expression control sequences. The need for, and identity of, expression control sequences will vary according to the type of cell in which the gp40 sequence is to be expressed. Examples of expression control sequences include transcriptional promoters, enhancers, suitable mRNA ribosomal binding sites, and sequences that terminate transcription and translation. Suitable expression control sequences can be selected by one of ordinary skill in the art. Standard methods can be used by the skilled person to construct expression vectors. See, generally, Sambrook et al., 1989, *Cloning—A Laboratory Manual* (2nd Edition), Cold Spring Harbor Press.

Vectors useful in this invention include plasmid vectors and viral vectors. Viral vectors can be those derived from retroviruses, adenovirus, adeno-associated virus, SV40 virus, or herpes viruses. Once introduced into a host cell (e.g., parasitic cell, bacterial cell, yeast cell, avian cell, mammalian cell), the vector can remain episomal, or be incorporated into the genome of the host cell.

In bacterial systems, a number of expression vectors may be advantageously selected depending upon the use intended for the gene product being expressed. For example, when a large quantity of such a protein is to be produced, e.g., for studying the interaction of a gp40 polypeptide with other proteins or for raising antibodies to the polypeptide, a vector capable of directing the expression of high levels of a fusion protein (e.g., a GST fusion protein) that is readily purified may be desirable. In general, such fusion proteins are soluble and can easily be purified from lysed cells by adsorption to, e.g., glutathione-agarose beads followed by elution in the presence of free glutathione.

Antibodies

The invention also includes antibodies specifically reactive with gp40 polypeptides, e.g., 4E9. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

Antibodies which specifically bind gp40 epitopes can also be used in immunohistochemical staining of a sample in order to evaluate the abundance and pattern of expression of gp40. Anti-gp40 antibodies can be used diagnostically in immuno-precipitation and immuno-blotting to detect and evaluate gp40 levels in tissue or bodily fluid as part of a clinical testing procedure.

Antisense gp40

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire gp40 coding strand, or to only a portion thereof, e.g., all or part of the protein coding region (or open reading frame). An antisense nucleic acid molecule can be antisense to a noncoding region of the coding strand of a nucleotide sequence encoding gp40. The noncoding region is the 5' and 3' sequences which flank the coding region and are not translated into amino acids (i.e., also referred to as 5' and 3' untranslated regions).

Given the coding strand sequences encoding gp40 disclosed herein (e.g., SEQ ID NO:3), antisense nucleic acids of the invention can be designed according to the rules of Watson and Crick base pairing. The antisense nucleic acid molecule can be complementary to the entire coding region of gp40 mRNA, but more preferably is an oligonucleotide which is antisense to only a portion of the coding or noncoding region of gp40 mRNA. For example, the antisense oligonucleotide can be complementary to the region surrounding the translation start site of gp40 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art.

The antisense nucleic acid molecules of the invention are typically administered to a subject infected with a microbe, e.g., *C. parvum*, such that they hybridize with or bind to cellular mRNA and/or genomic DNA of the microbe encoding a gp40 protein to thereby inhibit expression of the protein, e.g., by inhibiting transcription and/or translation. The hybridization can be by conventional nucleotide complementarily to form a stable duplex, or, for example, in the case of an antisense nucleic acid molecule which binds to DNA duplexes, through specific interactions in the major groove of the double helix. The antisense nucleic acid molecules can also be delivered to the microbe using the vectors described herein.

Screening Assays

The invention also encompasses methods for identifying compounds that modulate, e.g., inhibit or enhance, the expression of a gp40 gene or the activity of a gp40 polypeptide. These compounds can be used to prevent or treat pathogenesis of *C. parvum*. Candidate compounds that can be screened in accordance with the invention include nucleic acids, polypeptides, oligopeptides, antibodies, and monomeric organic compounds. In addition, fragments of gp40 are also good candidate compounds. Preferably the candidate compound inhibits the expression or activity of gp40.

With respect to identifying a compound which prevents pathogenesis of *C. parvum* (e.g., blocks the ability of *C. parvum* to bind to epithelial cells) it may be useful to first identify a compound that binds to gp40. Compounds identified for their ability to bind gp40 can then be subsequently tested in a secondary screen for their ability to inhibit the attachment and invasion of host cells by *C. parvum.*

Compounds of the present invention can be obtained using any of the numerous approaches in combinatorial library methods known in the art, including: biological libraries; spatially addressable parallel solid phase or solution phase libraries; synthetic library methods requiring deconvolution; and synthetic library methods using affinity chromatography selection. The library can be a peptide library, a non-peptide oligomer library, a small molecule library or a library of extracts from parasites, prokaryotes, or other organisms.

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad Sci. USA* 91:11422; Zuckermann et al. (1994). *J Med. Chem*. 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med Chem*. 37:1233.

An assay that can be used to identify a compound which binds gp40 is a cell-based assay in which a cell which expresses gp40, or a biologically active fragment thereof, is contacted with a candidate compound and the ability of the candidate compound to bind to gp40 or the biologically active fragment thereof is determined. The cell is preferably a microbial cell, e.g., a *C. parvum* cell. Although any type of cell which expresses gp40, e.g., one genetically engineered to express gp40, can be used instead. A cell which does not express gp40 is typically used as a control. Determining the ability of the candidate compound to bind to gp40 can be accomplished, for example, by coupling the candidate compound with a radioisotope or enzymatic label such that binding of the candidate compound to gp40 can be determined by detecting the labeled compound. In one embodiment, the amount of labeled compound bound to the cell is determined. Candidate compounds can be labeled with $^{125}$I, $^{35}$S, $^{14}$C, or $^{3}$H, either directly or indirectly, and the radioisotope detected by direct counting of radioemmission or by scintillation counting. Alternatively, candidate compounds can be enzymatically labeled with, for example, horseradish peroxidase, alkaline phosphatase, or luciferase, and the enzymatic label detected by determination of conversion of an appropriate substrate to product.

The present invention also features a cell-free assay comprising contacting a gp40 molecule or biologically active portion thereof with a candidate compound and determining the ability of the candidate compound to bind to gp40, or a biologically active portion thereof. Binding of the candidate compound to gp40 can also be determined by contacting gp40, or a biologically active portion thereof, with both a known gp40 ligand and a candidate compound. For example, the ability of the candidate compound to interact with gp40 is ascertained by determining if the interaction between .gp40 and the gp40 ligand is decreased. A decrease in interaction is an indication that the candidate compound binds to gp40.

Alternatively, the cell-free assay can be carried out by contacting gp40, or a biologically active portion thereof, directly with a candidate compound, and determining the ability of the candidate compound to interact with gp40. It may be desirable to immobilize either gp40 or the candidate compound to facilitate separation of gp40-candidate compound complexes from uncomplexed forms. For example, glutathione-S-transferase-gp40 (GST-gp40) fusion proteins can be prepared by standard recombinant techniques and then adsorbed onto glutathione sepharose beads (Sigma Chemical; St. Louis, Mo.) or glutathione derivatized microtitre plates. The candidate compound is incubated with immobilized GST-gp40 under conditions conducive to complex formation between the gp40 and the candidate compound (e.g., at physiological salt, temperature and pH conditions). Following incubation, the beads or microtitre plate wells are washed to remove any unbound components and gp40-candidate complex formation is determined.

Other techniques for immobilizing proteins on a solid matrix can also be used in the screening assays of the invention. For example, gp40 or the candidate compound can be immobilized utilizing conjugation of biotin and streptavidin. Biotinylated gp40 or biotinylated candidate compounds can be prepared from biotin-NHS (N-hydroxysuccinimide) using techniques well known in the art (e.g., biotinylation kit, Pierce Chemicals; Rockford, IL), and immobilized in the wells of streptavidin-coated 96 well plates (Pierce Chemical). Alternatively, antibodies reactive with gp40 can be immobilized on the wells of the plate by standard techniques, and used to trap gp40.

Secondary Screens

A candidate compound which binds to gp40 may be further tested in order to identify its specific biological activity. One approach will be to determine if the candidate compound can competitively inhibit attachment of native gp40 proteins of *C. parvum* to a host cell. For example, this assay includes growing cells to which *C. palvum* sporozites bind and invade, e.g., Caco-2A cells, in 96 well plates and fix with glutaraldehyde to prevent invasion. Purified sporozoites or Caco-2 cells are then pre-incubated with putative candidate compounds for 30 min at 4° C. and then incubated together for one hour at 37° C. Unattached sporozoites will be washed off and bound sporozoites quantified by ELISA. The attachment assay will assess the ability of the candidate compound to inhibit adherence of sporozoites to host cells, either by blocking specific parasite adhesions or by competitively binding to receptor sites on host cells (Verdon el al., The J Infect Dis. 175:1268–1272).

An assay to determine whether a compound can inhibit infection of a host cell by C. parvum may also be preformed. Oocysts or confluent Caco-2A monolayers in 96 well plates are pre-incubated with candidate compound or controls for 30 min at 4° C. and then incubated for 24 hours at 37° C. Cells are washed, fixed and permeabilized with methanol and intracellular parasites quantified by ELISA. The infection assay will assess the effect of a candidate compound on attachment as well as subsequent invasion and intracellular development.

A compound which inhibits the attachment and/or infection of a host cell by C. parvum in vitro, can be further tested for its ability to inhibit attachment and infection in vivo using a crptosporidosis mouse model. For example, the candidate compound can be administered to a mouse which is infected with C. parvum. Alternatively, the compound can be administered to a mouse which is free of C. parvum and which subsequent to administration of the compound is infected with C. parvum. The ability of the compound to inhibit infection by C. parvum is determined by measuring oocyst shedding of faecal suspension, e.g., between day 4 and 9 after administration of $1 \times 10^5$ oocysts/mouse. In addition, measuring the weight of mice following infection is preformed as significant weight loss is indicative of infection by the parasite. Histological studies of the small intestinal epithelium is preformed to reveal if the parasite is colonizing the small intestinal epithelium.

Methods of Treatment

The invention features a method for treating a subject, e.g., a human, infected with a protozoan, e.g., a C. parvum. The method can include the step of administering to the subject a compound that inhibits gp40 activity. Such compounds include wild-type gp40 or a nucleic acid encoding either of them; an active fragment of gp40 or a nucleic acid encoding them; a gp40 antisense molecule; a gp40 antibody; a gp40 inhibitor, e.g., a small molecule or drug identified using the screening assays described above, which inhibits gp40 protein activity; and an inactivated e.g., truncated gp40 polypeptide that binds to gp40 binding sites on host cells, thereby acting as a competitive inhibitor of gp40 expressed on the surface of C. parvum.

The gp40 nucleic acid molecules, proteins, modulators, of the invention can be incorporated into pharmaceutical compositions suitable for administration to a subject, e.g., can be used to treat an individual with C. parvum infection. Such compositions typically include the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound.

The pharmaceutical compositions can be included in a container, pack, or dispenser together with instructions for administration.

Diagnostic Assays

The invention further provides a method for detecting and identifying C. parvum in a sample, e.g., a biological sample such as serum or a tissue sample. The method involves contacting the sample with a compound or an agent capable of detecting gp40 protein, DNA or mRNA such that the presence of gp40 is detected in the biological sample. A preferred agent for detecting gp40 mRNA, is a labeled or labelable nucleic acid probe capable of hybridizing, to gp40 mRNA. The nucleic acid probe can be, for example, the full-length gp40 nucleotide sequence of SEQ ID NO:3 or portions thereof, such as an oligonucleotide of at least 15, 30, 50, 100, 205, 210, 220, 250 or 500 nucleotides in length and sufficient to specifically hybridize under stringent conditions to a gp40 DNA or mRNA. The gp40 nucleic acid molecule can be detected by using a labeled or labelable nucleic acid probe capable of hybridizing to gp40 DNA or mRNA and/or nucleic molecules generated by the polymerase chain reaction. Primers used in the polymerase chain reaction can be designed based on SEQ ID NO:3. Designing primers for amplification purposes is well known in the art. A preferred agent for detecting gp40 protein is a labeled or labelable antibody capable of binding to gp40 protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "sample" is intended to include any sample including biological samples (e.g., tissues, cells, e.g., intestinal cells, or feces) and fluids (e.g., surface water). The detection method of the invention can be used to detect gp40 DNA, mRNA or protein, in a biological sample in vitro as well as in vivo. For example, in vitro techniques for detection of gp40 mRNA include Northern hybridizations and in situ hybridizations. In vitro techniques for detection of gp40 protein include enzyme linked immunosorbent assays (ELISAs), Western blots, immunoprecipitations and immunofluorescence. Alternatively, gp40 protein can be detected in vivo in a subject by introducing into the subject a labeled anti-gp40 antibody. For example, the antibody can be labeled with a radioactive marker whose presence and location in a subject can be detected by standard imaging techniques.

It will be understood by one skilled in the art that when any of the methods above are being applied to cells or organisms, rather than to nucleic acids derived from them, it will be necessary to incorporate a procedure for liberating nucleic acids from the cells or organisms before, e.g., initiating amplification chain reaction conditions. The preferred forms of the present invention provide particular procedures whereby the sample to be tested is first suspended in a medium, e.g., a buffer, and then either sonicated or subjected to freeze/thaw cycles in buffer containing a reducing agent, e.g., dithiothreitol (DTT) in order to rupture the cells or organisms (particularly their oocyst forms) and liberate the polynucleic acids.

The invention also encompasses kits for detecting the presence of gp40 in a biological sample. For example, the kit can include a labeled or labelable compound or agent capable of detecting gp40 protein, DNA or mRNA in a biological sample. The compound or agent can be packaged in a suitable container. The kit can further include instructions for using the kit to detect gp40 mRNA or protein.

EXAMPLES

Example 1

MAb 4E9 Neutralizes C. parvum infection of Intestinal Epithelial Cells and Inhibits Sporozoite Attachment to These Cells in vitro This example details the generation of an antibody against a C. parvum sporozoite and the use of this antibody to inhibit sporozoite attachment to a cell.

In order to identify putative C. parvum adhesion/invasion-specific proteins, MAbs to sporozoites were generated.

Sporozoites were purified by isopycnic Percoll gradient centrifugation (Arrowood el al. (987) J. Parasitol. 73:314–3319) or by filtration through a 2.0 µm Nucleopore polycarbonate filter (Costar Scientific Corporation, Cambridge, Mass.). Shed proteins (SP) were obtained by excystation of oocysts in DMEM for 2 h at 37° C., followed by centrifugation at 5000×g, at 4° C. for 10 min Protease inhibitors (final concentration: 2 mM PMSF, 20 µM leupeptin, 10 µM E64, 2 mM EDTA) were added to the supernatant which was concentrated 10-fold by ultrafiltration. SP were identified by SDS PAGE and silver staining. BALB/c mice were immunized intraperitoneally with C. parvum sporozoites, spleen cells fused with myeloma cells and hybridomas cloned in liquid medium were generated. The antibodies were screened by immunofluorescence to identify clones reactive with the surface or anterior portion of sporozoites (suggestive of an apical complex localization).

For initial screening of MAbs purified oocysts and sporozoites were placed on a 10-well glass slide pre-coated with ovalbumin (1mg/ml in PBS) and air-dried at room temperature (RT). For localization of the epitope recognized by MAb 4E9, purified oocysts were placed on poly-L-lysine (30 ptg/ml in water)-coated slides and excysted for 30 min at RT. Purified sporozoites were allowed to glide on poly-L-lysine-coated slides for 30 min at RT. For intracellular stages, Caco-2A cells were infected with oocysts for 24 h as described in Verdon el al. ((997) J. Infect Dis. 175:1268–1272). Slides with oocysts and sporozoites were fixed with methanol or 4% paraformaldehyde for 10 min at RT. Slides with intracellular stages were fixed and permeabilized with methanol and immunoflouresence was performed. Controls included culture medium and the irrelevant IgM MAb B9A4.

Using this approach, 4E9, an IgM MAb, was identified. To determine whether proteins recognized by 4E9 were involved in initial host-parasite interactions, the effect of this MAb on invasion and intracellular development of C. parvum in vitro was evaluated. This effect was studied by a modification of an in vitro assay described in Verdon et al. (supra). Briefly, Caco-2A cells ($2 \times 10^4$/well) were grown for 48 h in 96-well tissue culture plates. Oocysts ($10^4$/well) were pre-incubated with 4E9 or B9A4 IgM for 30 min at RT and incubated with the cells for 24 h at 37° C., 5% $CO_2$. Cells were fixed and permeabilized with methanol for 10 min at RT and washed 3 times with TBS. Infection was quantified by ELISA as described by Verdon et al. (supra).

Figure 7A:
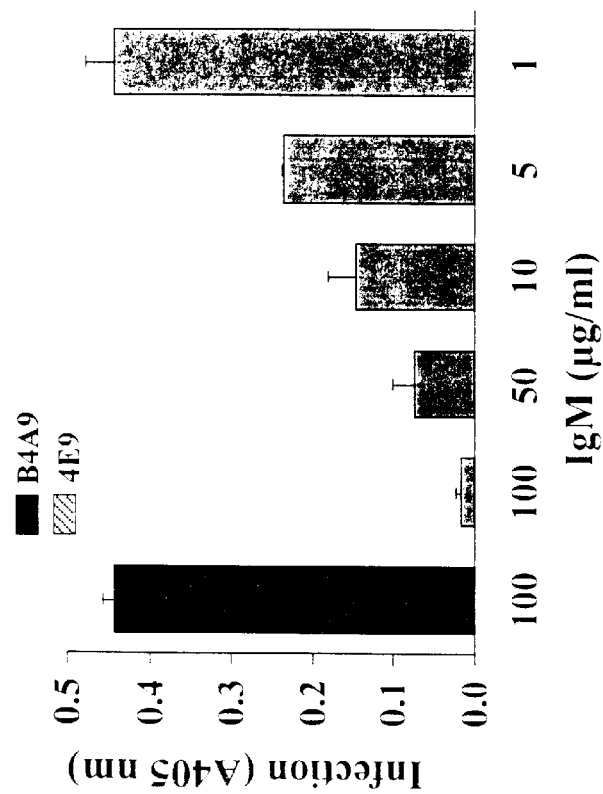

When compared to that of an irrelevant control MAb, 4E9 IgM neutralized infection of Caco-2A cells in a dose-dependent manner with almost complete inhibition occurring at a concentration of 100 µg/ml (FIG. 7A). The inhibition of infection was not due to toxicity of 4E9 for host cells, since the MAb had no effect on viability.

The 4E9 MAb inhibited sporozoite attachment to fixed Caco-2A cells in a dose dependent manner, with 50% inhibition at 100 µg/ml (FIG. 7B), suggesting that the neutralizing effect of this MAb on infection is at least in part mediated by blocking adherence.

Example 2

The Protein Recognized by 4E9 is Present in Multiple Developmental Stages

An immunoflouresence assay was used to identify the epitope recognized by 4E9 at various developmental stages including oocysts, sporozoites and intracellular stages.

Oocysts (GCHI) maintained by passage in calves and purified as described in Arrowood et al. ((1987) *J. Parasitol.* 73:314–319) were treated with 1.75% (v/v) sodium hypochlorite for 10 min on ice, washed with DMEM (Life Technologies, Grand Island, N.Y.) containing 25 mM HEPES, 100 U/ml penicillin, 100 ug/ml streptomycin and excysted for 1 h at 37° C. in the presence of 0.25% trypsin and/or 0.75% taurocholic acid. 4E9 reacted with material shed from oocysts that were undergoing excystation as well as with the surface of newly excysted sporozoites. In addition, 4E9 reacted with the surface and apical region of purified sporozoites as well as with material shed in trails. These results suggested that one antigen recognized by 4E9 is present on one surface of sporozoites as well as in apical complex organelle.

In addition, 4E9 reacted with intracellular stages including meronts present in infected Caco-2A cells. Merozoites within the meronts or newly released from them appeared to be stained along the entire surface. These findings were confirmed and extended by immunoelectron microscopy (IEM).

Piglets and IFN-γ-knockout mice were infected with *C. parvum* as described in Tzipori et al. ((1981) *Res. Vet. Sci.* 31:358–368). Intestinal tissue, oocysts and sporozoites were fixed in 0.25% glutaraldehyde, 4% paraformaldehyde in 0.1 M sodium phosphate buffer, pH 7.2 (PB) at 4° C. overnight. Oocysts and sporozoites were pelleted by centrifugation, 2% agarose was added and allowed to solidify. Samples were washed with PB, dehydrated in graded ethanol series to 95%, and embedded in L.R. White Resin (Electron Microscopy Sciences, Fort Washington, Pa.). Silver-gold sections from polymerized blocks were placed on formvar coated 300 mesh nickel grids. Grids with sections were floated on drops of 0.05 M glycine, 0.5 M NaCl, 1% Tween 20, 0.05 M Tris, pH 7.5 (TBST) for 30 min; 1% bovine serum albumin (BSA) in TBST for 10 min; 10% NGS in TBST for 10 min. Grids were then placed on 4E9 IgM 10 or 100 µg/ml or normal mouse serum diluted 1:10 or 1:100 at 4° C. for 1 h. The grids were next placed on 1% BSA in TBST for 5 min and then placed for 30 min on a 1:10 dilution of 10 nm colloidal gold conjugated to goat anti-mouse Ig, diluted in 5% BSA, 1% NGS in TBST. The grids were then washed, stained with 3% aqueous uranyl acetate and viewed by transmission electron microscopy.

Results show that 4E9 binding was detected at the surface of sporozoites and in locations surrounding the sporozoite, consistent with shedding of the protein from the surface. Apical complex organelles were not visualized in this preparation. In oocysts, 4E9 binding was localized on the surface of sporozoites. Examination of meronts in infected pig ileum revealed labeling on the surface of merozoites. In addition, there was reactivity with microgametes in INF-γ-knockout mouse infected intestine.

Example 3

MAb 4E9 Recognizes 2 Major *C. parvum* Peptides >900 and 40 kDa in $M_r$

This example details that the MAb 4E9 recognizes two *C. parvum* proteins, one has a molecular weight of 900 kDa and the other protein has a molecular weight of 40 kDa.

The epitope recognized by MAb 4E9 was present on 2 major bands by immunoblotting; a 40,000 $M_r$ peptide, and a very high molecular weight peptide >200,000 in $M_r$. This latter peptide co-migrated with a previously described >900.000 $M_r$ glycoprotein (GP900) recognized by MAb 7B3 (Petersen, C. et al. (1992) *Infect Immun.* 60:5132–5138). Oocyst/sporozoite proteins immunoprecipitated by MAb 7B3 were recognized by 4E9 by immunoblotting, confirming that this peptide was GP900.

For immunoblot analysis, oocysts, sporozoites and SP were solubilized in reducing sample buffer, separated by 5–15% gradient SDS PAGE and transferred to nitrocellulose for 18 h at 395 mA at 4° C. Bound proteins were probed with MAb 4E9 and detected by chemiluminescent or calorimetric methods. For the chemiluminescent method, non-specific binding was blocked with 10% NGS in 10 mM Tris-HCl, 150 mM sodium chloride, pH 8.0 (TBS) for 1 h before incubation with MAb 4E9 in 5% NGS in 0.1% Tween 20 in TBS (0.1% T-TBS) for 90 min at RT. After washing three times with 0.1% T-TBS, strips were incubated with horseradish peroxidase conjugated goat anti-mouse antibody (Immunopure, Pierce) diluted in 5% NGS-0.1% T-TBS for 1 h at RT. Strips were washed, incubated in SuperSignal substrate (Pierce), exposed to film and developed. For the calorimetric method, non-specific binding was blocked with 5% non-fat milk (NFM) in TBS for 1 h before incubation with MAb 4E9 in 1% NFM in TBS for 1 h at RT. After washing with 0.05% T-TBS, strips were incubated with alkaline-phosphatase-conjugated goat anti-mouse antibody (Promega, Madison, Wis.) in 1% NFM in TBS for 1 h at RT. Strips were washed and developed with nitroblue tetrazolium (NBT) 5-bromo-4-chloro-3-indolyl phosphate (BCIP) substrate.

Immunoprecipitation was carried out as follows. A mixture of sporozoites and oocysts in PBS containing protease inhibitors (final concentration: 2 mM PMSF, 20 µM leupeptin, 10 µM E64, 2 mM EDTA) were lysed by 5 freeze-thaw cycles and detergent extraction with 1% Triton X-100. The lysate was centrifuged at 10,000×g for 30 min. Detergent soluble material was incubated with MAb 7B3 overnight followed by incubation with Protein G Sepharose (Pharmacia Biotech Inc.) for 2 h at 4° C. After extensive washing with 20 mM phosphate, 0.5 M NaCl, 0.5% Triton X-100, 0.1% SDS, 0.1% deoxycholate, immunoprecipitated proteins were analyzed by SDS-PAGE and immunoblotting with MAb 4E9 (see above). GP900 and the 40,000 $M_r$ protein (designated gp40) were present in oocysts and sporozoites. An additional 250,000 $M_r$ protein was also detected only in oocysts. Analysis of SP by SDS PAGE and silver staining revealed the presence of 5 major bands; >900,000; 120,000; 55,000; 40,000 and 35,000 $M_r$. Two of these, GP900 and gp40 were recognized by MAb 4E9 by immunoblottinig. Since this preparation, was enriched for these two proteins it was used for further characterization of the epitope recognized by 4E9.

Example 4 gp40 is Unrelated to GP900

This example shows that gp40 is unrelated to gp900.

The presence of these αGalNAc residues was exploited to purify glycoproteins gp40 and gp900 from *C. parvum* lysates by HPA-affinity chromatography as follows. Hypochlorite-treated oocysts (1–2×10⁸/ml)in PBS containing protease inhibitors (described above) were lysed by 5 freeze-thaw cycles followed by detergent extraction with 1% octylglucoside in PBS (OGS-PBS). Detergent soluble material was incubated with HPA-agarose (EY Laboratories, Inc., Sari Mateo, Calif.) in 1%OGS-PBS, for 18 h at 4° C. After extensive washing, bound proteins were eluted with 0.1 M GalNAc in 0.05%OGS-PBS.

Analysis of this preparation by silver staining and immunoblotting with 4E9 revealed that a 40 kDa band recognized by MAb 4E9 was among the major proteins present (bands at >900, 128, 26, and 13 kDa were also present). The 40 kDa band was subsequently confirmed to be gp40 by N-terminal sequencing of the first 5 residues.

In order to produce gp40-specific antibodies, the 40 kDa band was excised from a polyacrylamide SDS gel and used to immunize mice. Following excision, gp40 was lyophilized and emulsified with complete Freund's Adjuvant for the initial immunization and incomplete complete Freund's Adjuvant for subsequent boosts. BALB/c mice were immunized at 3–4 week intervals with this material and the presence of anti-gp40 antibodies in sera monitored by immunoblotting of an oocyt/sporozoite antigen preparation. Antisera from these mice reacted exclusively with a 40 kDa band by immunoblotting. The polyclonal anti-gp40 sera immunoprecipitated a 40 kDa band from *C. parvum* sporozoite/oocyst lysates which was recognized by MAb 4E9, confirming that both antibodies recognized the same protein. There was no reactivity with GP900 suggesting that other than the presence of a common carbohydrate epitope, gp40 is unrelated to GP900.

Example 5 gp40-specific Antisera Neutralize *C. parvum* Infection of Intestinal Epithelial Cells This example shows that gp40-specific antisera neutralize *C. parvum* infection.

Figure 8:
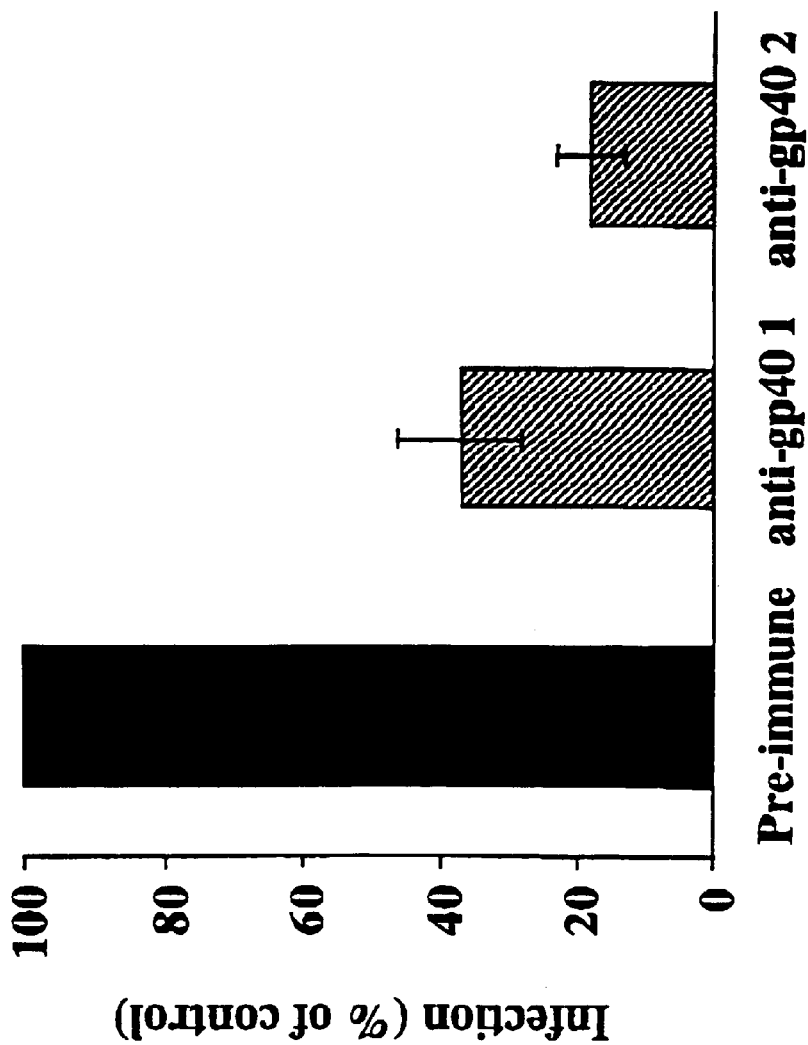
FIG. 8 is a histogram depicting the effect of gp40-specific antisera on neutralizing C. parvum infection of intestinal epithelial cells. Results are expressed as a percentage of the control. A control using pre-immune serum is also depicted.

In order to determine if gp40 is involved in mediating attachment and/or invasion the effect of the gp40-specific antisera on *C. parvum* infection of intestinal epithelial cells was assessed using an ELIZA-based in vitro assay which was previously described (Verdon et al., supra, 1997). Compared to the pre-immune serum, gp40-specific antisera (from 2 different mice) significantly inhibited *C. parvum* infection of Caco-2A cells, implicating gp40 in *C. parvum* attachment to and/or invasion of host cells (FIG. 8).

Example 6

Proteins Recognized by 4E9 bind to Intestinal Epithelial Cells

Figure 9:
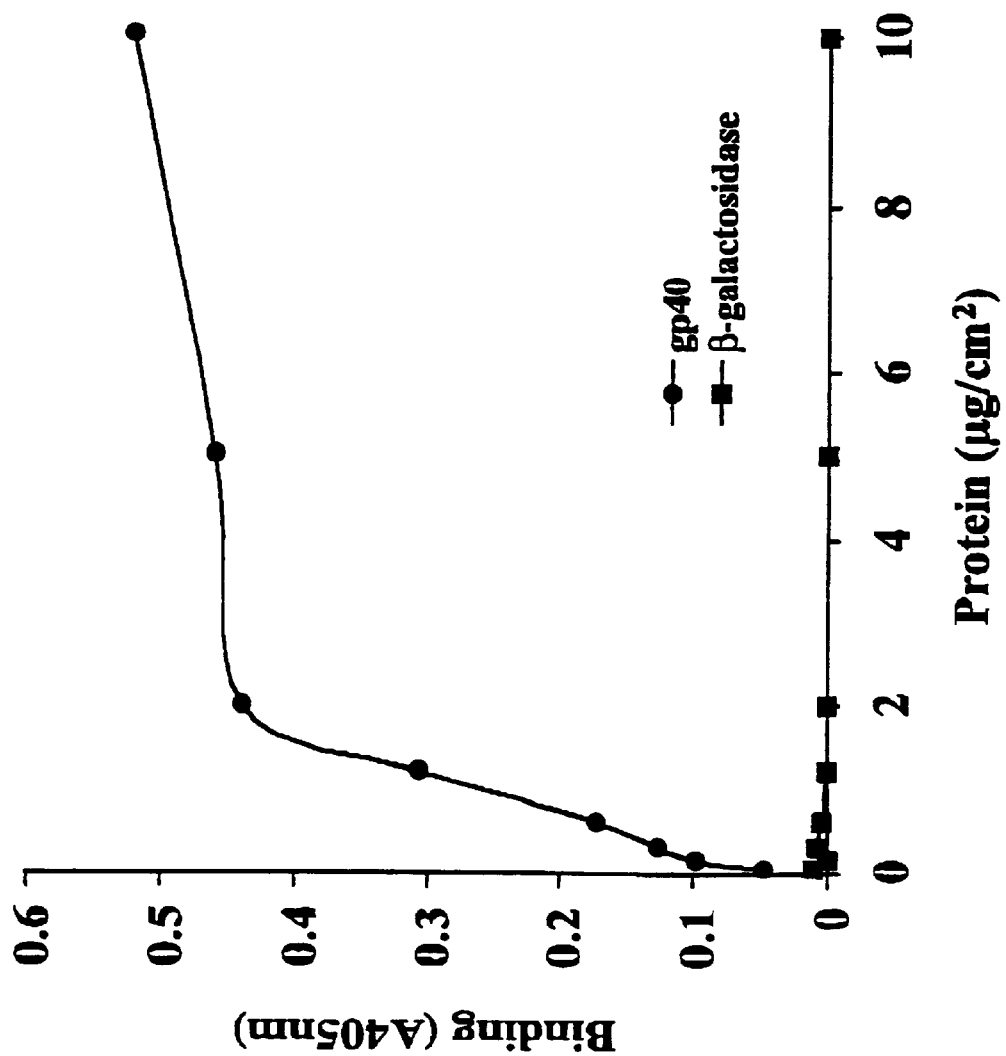
FIG. 9 is a graph showing binding of gp40 to intestinal cells. Binding by the control is also shown.

This example shows that the proteins recognized by 4E9 bind to intestinal epithelial cells. Inhibition of sporozoite attachment to intestinal cells suggested that proteins recognized by 4E9 might be involved in attachment. To confirm this finding, shed proteins (enriched in GP900 and gp40) were incubated with Caco-2A cells and attachment of these proteins to the cells quantified by 4E9 binding by ELISA. As seen in FIG. 9, binding of the proteins recognized by 4E9 occurred in a dose-dependent and saturable manner. There was no binding of the control glycoprotein ovalbumin. Binding occurred to fixed as well as live cells. This result further suggested that GP900 and/or gp40 are involved in sporozoite attachment to host cells.

Example 7

Epitope Recognized by 4E9 is Glycosylated and Contains α-linked GalNAc Residues

This example shows that the epitope recognized by 4E9 is glycosylated and contains α-linked GalNAc residues.

Reactivity of 4E9 with GP900 and gp40 was abolished by mild periodate treatment suggesting that the epitope is glycosylated. In order to determine the nature of the carbohydrates present, SP were probed with a panel of biotinylated lectins of varying sugar specificity (Table 1). Of these, HPA, SBA, AIA, MPA, UEA-1 and WGA bound to both GP900 and gp40, whereas Con A and DBA bound to GP900 but not gp40. Binding was specific since it could be inhibited by the appropriate cognate sugar hapten. Of note was the binding of a number of αGalNAc specific lectins. The pattern of reactivity of αGalNAc-specific lectins such as 1-IPA was identical to that of 4E9. In addition, reactivity of 4E9 could be competitively inhibited by HPA. These results suggested that the epitope recognized by 4E9 contains the same carbohydrate residues as that bound by the αGalNAc-specific lectins.

In order to determine the nature of the glycosidic linkage of the saccharides in the epitope recognized by 4E9, SP were treated with specific glycosidases and probed with 4E9 by immunoblotting. Treatment with PNGase F (which cleaves N-linked glycans) had no effect on 4E9 reactivity. Treatment with endo-α-N-acetyl-galactosaminidase which is specific for Galβ1-3GalNAc linked to Ser or Thr also had no effect suggesting that a) this disaccharide is not part of the epitope recognized by 4E9, or b) if it is present that it is substituted with sialic acid, fucose or GalNAc residues. Treatment with increasing concentrations of α-N-acetyl-galactosaminidase, which cleaves terminal α1-3GalNAc or GalNAcα 1-Ser/Thr from O-linked glycoproteins resulted in decreasing reactivity with both 4E9 as well as the lectin HPA and a shift to 36 kDa in $M_r$ of gp40. This effect was specific since it could be inhibited by the substrate pNP α-N-acetyl-galactosaminide. These results suggest that GP900 and gp40 contain αGalNAc residues and that these residues are terminal in gp40.

To investigate the possibility that αGalNAc residues present in the epitope recognized by 4E9 are involved in attachment, we first determined whether lectins specific for these residues bound to sporozoites. The results showed that the lectins HPA, MPA and AIA all bound to the surface and apical region of sporozoites in a pattern similar to that of MAb 4E9. The binding was specific since it could be inhibited by pre-incubation with the cognate sugar hapten. We next determined the effect of these lectins on sporozoite attachment to host cells. The results showed that all three αGalNAc-specific lectins significantly inhibited attachment at a concentration of 10 μg/ml, whereas lectins such as SNA which did not bind to sporozoites or to GP900 and gp40 (Table 1) had no significant effect. Since the lectins were washed off after preincubation with the sporozoites, the inhibitory effect was not due to binding of the lectins to the host cells. These results strongly implicate the αGalNAc residues of GP900 and /or gp40 in mediating sporozoite attachment to host cells.

TABLE 1

| Lectin | Monosaccharide Specificity | Oligosaccharide Specificity | GP900 | gp40 |
|---|---|---|---|---|
| *Helix pomatia* agglutinin | αGalNAc | Tn[A], T[B], F[C], A[D] | + | + |
| *Dolichos biflorus* agglutinin | αGalNAc | F, A | + | − |
| *Artocarpus integrifolia* agglutinin | αGal, αGalNAc | Tn, T | + | + |
| *Glycine max* agglutinin | α (β) GalNAc, Gal | Tn, A | + | + |
| *Maclura pomifera* agglutinin | αGalNAc, αGal, | Tn, T, | + | + |
| *Arachis hypogea* agglutinin | βGal | T | − | − |
| *Sophora japanicum* agglutinin | βGalNAc, Gal | T, | − | − |
| *Ulex europeus* agglutinin-1 | αL-Fuc | Fuc α1-2Galβ1-4GlcNAc | + | + |
| *Canavalia ensiformis* agglutinin | Glc, Man | Branched man | + | − |
| *Triticum vulgare* agglutinin | GlcNAc | GlcNAcβ1-4GlcNAc | + | + |
| *Sambucus nigrans* agglutinin | Neu5NAc, βGal | Neu5NAc α2-6 Gal | − | − |
| *Maakia amurenis* agglutinin | Neu5NAc | Neu5NAc α2-3 Gal | − | − |

[A]Tn, GalNAc α1-Ser/Thr; [B]T, Galβ1-3GalNAc; [C]F, GalNAcα1-3GalNAc; [D]A, GalNAcα1-3Gal

Example 8

Cloning, Sequencing and Expression of the Gene Encoding gp40

This example describes the cloning and sequencing of the gene encoding gp40.

The strategy was to ascertain the N-terminal and internal amino acid sequences from 2 internal tryptic peptides of native gp40 (purified from shed proteins by size exclusion ultrafiltration and gel-isolation) and design degenerate PCR primers based on these peptide sequences to amplify the gene encoding gp40.

The N-terminal 5 amino acids and two internal tryptic peptides designated p70 and p81 were sequenced. Comparison of these sequences with the deduced amino acid sequence of GP900 (Barnes et al., Mol. Biochem. Parasitol. 96:93–110, 1998) using the BLAST (Altschul et al., Nucleic Acid Res. 25:3389–402, 1997) program, revealed no significant similarity, confirming that these two proteins are unrelated. In addition, BLAST searches (Altschul et al., supra, 1997) with these sequences did not reveal significant similarity with known proteins in the databases. The sequence of the N-terminal 5 amino acids of gp40 isolated by HPA affinity chromatography was identical to that isolated from shed proteins, confirming that both preparations contained the same protein.

Figure 10:
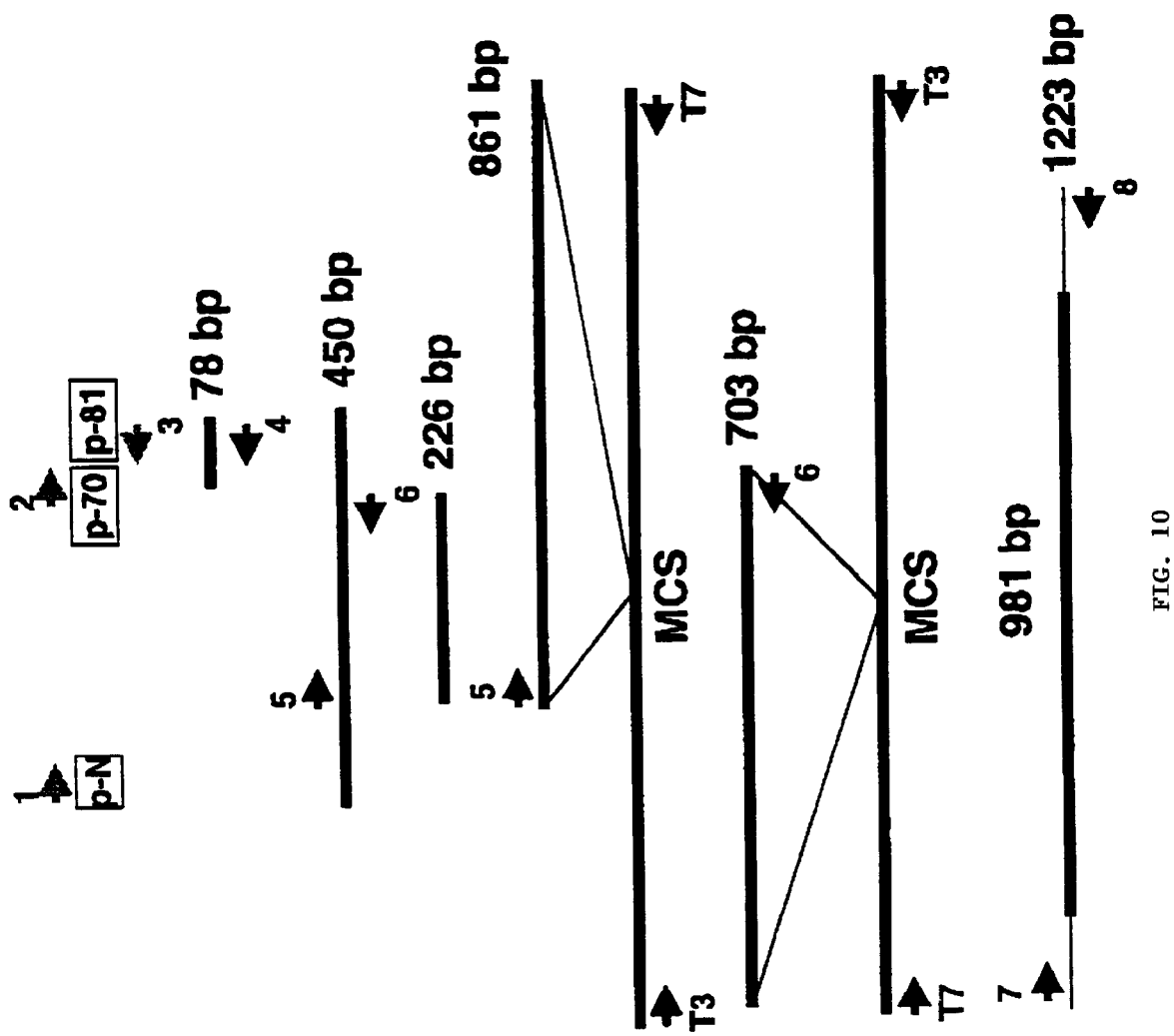
FIG. 10 depicts the multiple PCR steps that were used to clone the gene encoding gp40.

The multiple PCR steps that were used to clone the gene encoding gp40 (FIG. 10). Using degenerate primers 2 and 3 based on the amino acid sequence of internal peptides p70 and p81, a 78 bp fragment was amplified from oocyst genomic DNA, cloned into a vector and sequenced. Using primer 4 (based on the nucleotide sequence of the 78 bp fragment) and degenerate primer 1 (based on the amino acid sequence of the N-terminal peptide) a 450 bp product was amplified from the same oocyst genomic DNA, cloned and sequenced. The deduced amino acid sequences of the 78 and 450 bp fragments matched those of the known peptide sequences from the native protein. Primers 5 and 6 (based on the nucleotide sequence of the 450 bp fragment were used to screen six *C. parvum* genomic and cDNA libraries by PCR. A product of the expected size (226 bp) was amplified from all of the libraries tested. Anchored PCR of one of these libraries (GCHl, genomic DNA in λZap II) was used to obtain the 5' and 3' sequences of the 450 bp fragment. Thus, DNA from this library was used as a template for PCR with primers based on the sequence of the T7 promoter of the λZap IT phage vector (primer T7) and the 450 bp fragment (primer 5). The resulting 861 bp product amplified by PCR was sequenced. A similar approach was used with primer 6 to obtain a 703 bp product. Assembly and analysis of these overlapping fragments revealed a 981 bp ORF. Subsequently, a 1223 bp fragment was amplified by PCR from oocyst (GCHl) genomic DNA. using primers 7 and 8 along with a high fidelity polymerase pfu (Stratagene, La Jolla, Calif.) and cloned into the Topo pCR vector. Four independently derived clones were sequenced to correct potential PCR errors. BLAST comparison of the DNA and deduced amino acid sequences with protein and nucleic acid databases did not reveal significant similarity with any known genes or proteins.

Analysis of the deduced amino acid sequence revealed a 326 amino acid protein with a calculated $M_r$ of 33.6 kDa (FIG. 2). The amino acid sequence corresponding to the N-terminus of the native protein was found 30 amino acids after the start codon. This hydrophobic stretch of 30 amino acids at the N-terminal region is consistent with a signal peptide. Hydropathicity analysis revealed hydrophobic regions at both the amino and carboxy termini. Of note was a contiguous stretch of 19 serine residues in the N-terminal region of the mature protein. There was a short hydrophobic region at the C-terminus, consistent with that required for addition of a GPI anchor. Thirty-two threonine and serine residues in the deduced amino acid sequence of gp40 are predicted to be sites of mucin type O-glycosylation. A single potential N-glycosylation site was also identified.

Example 9

The Gene Encoding gp40 is Present in a Single Copy and Does not Contain Introns This example shows that gp40 is a single copy gene which does not contain introns.

Southern blot analysis of genomic DNA isolated from GCHl oocysts using an 856 bp probe indicated that this sequence is present in a single copy in the *C. parvum* genome. This probe hybridized to a single approximately 800 bp EcoRI/Hind III restriction fragment of the expected size. When genomic DNA was digested with EcoRI alone the probe hybridized to a single 23 kb fragment.

Reverse transcriptase PCR analysis using primers 9 and 10 (which span 949 bp of the gp40 ORF) of RNA obtained from *C. parvum* intracellular stages, revealed a product of the same size as the product obtained by PCR of genomic DNA using the same primers. This finding suggests that the gene encoding gp40 does not contain introns.

Example 10

The Gene Encoding gp40 also Encodes a 15 kDa Glycoprotein (gp 15)

This example shows that gp40 encodes gp15.

In an independent study, MAbs CrA1 and CrA2 which recognize a previously identified 15 kDa surface glycoprotein (Gut and Nelson, J. Eukaryot. Microbiol, 1994) were used to isolate a clone from a genomic DNA expression library (Strong, et al personal communication). Analysis of the DNA sequence of this clone revealed that it was almost identical to that of the gene identified in the present study. The possibility that the gene encoding gp40 also encoded a 15 kDa protein (named gp15) was investigated. Previous studies indicated that gp15 bound the lectin HPA suggesting that this protein may be present in the HPA-purified glycoprotein preparation used to isolate native gp40. Analysis of this preparation by SDS-PAGE and immunoblotting with MAb CrA1 indicated that a 13 kDa protein recognized by Mab CrA1 was indeed present. N-terminal sequence information was obtained on gp15. The results indicated that the N-terminal residues ETSEA, corresponded to amino acid residues 223–227 of the deduced amino acid sequence of the gene encoding gp40. This finding indicates that gp15 is encoded by the same gene as gp40.

Example 11 gp40 and gp15 are Antigenically Distinct Proteins Encoded by the Same Gene

This example shows that gp40 and gp15 are antigenically distinct proteins.

To characterize the relationship between gp40 and gp15, it was determined whether antibodies to gp40 and gp15 cross-reacted with the respective native proteins by immunoblotting of various *C. parvum* preparations. The results indicated that anti-gp40 sera reacted with a 40 kDa band and MAb CrA1 reacted with a 15 kDa band in all the antigen preparations tested with no cross-reactivity between them. There was no difference in molecular weight of either protein under reducing or non-reducing conditions. To further corroborate these findings, fragments of gp40 and gp 15 proteins were over-expressed, e.g., amino acids 31–326 (corresponding to the entire ORF minus the signal peptide; designated pAMC40/15; SEQ ID NO:2), amino acids 31–222 (corresponding to gp40; designated pAMC40) and amino acids 223–326 (corresponding to gp15, SEQ ID NO:8; designated pAMC15) in *E. coli*. These thioredoxin fusion proteins were probed with gp40 and gp15-specific antibodies. The results showed that both antibodies reacted with the fusion protein encoded by the entire ORF. However, the anti-gp40 antibody reacted only with the fusion protein encoded by pAMC40 and MAb CrA1 reacted only with the fusion protein encoded by pAMC15. These results confirm that gp40 and gp15 are antigenically distinct proteins, which are both encoded by the same gene gp40.

To determine if peptides corresponding to gp15 were present in native gp40, the MS/MS spectra of peptides obtained after tryptic digestion of gp40 was analyzed using the algorithm Sequest. All 6 peptides (derived from gp40) analyzed on two separate occasions were represented in the portion of the deduced amino acid sequence of gp40 present in the N-terminal 222 residues. In contrast, none of the peptides corresponded to the amino acids present in residues 223–326 of gp15. This result confirms that gp40 and gp15 are distinct polypeptides.

Example 12 gp40 and gp15 are Products of Proteolytic Cleavage of a Precursor Protein

This example demonstrates that gp40 and gp15 are proteolytic fragments of a larger precursor protein (FIG. 6).

It was determined whether a putative precursor protein was expressed by intracellular stages of the parasite during merogony. To do this CACO-2A cells with oocysts were infected for 12 hours and isolated αGalNAc-containing glycoproteins from them by HPA-affinity chromatography. Analysis of these glycoproteins by immunoblotting with antibodies specific for gp40 and gp15 revealed the presence of a 50 kDa protein which was recognized by both antibodies, in addition to 40 kDa and 15 kDA bands recognized only by anti-gp40 antisera and MAb CrA1, respectively. There was no reactivity of either antibody with glycoproteins isolated in the same way from uninfected cells. These results implicate the 50 kDa protein recognized by both antibodies as the precursor and confirm that gp40 and gp15 are proteolytic fragments of the same protein.

Example 13 gp40 and gp15 are Differentially Localized in Invasive Stages of *C. parvum*

In this example antibodies specific for both gp40 and gp15 were used to determine the localization of gp40 and gp15 in *C. parvum* during developmental stages by immunofluorescence (IF).

The anti-gp40 antisera reacted mainly with the surface of the anterior portion of sporozoites, suggestive of an apical complex localization. In intracellular stages, there was reactivity with the entire surface and the apical region of merozoites (present within meronts) in infected Caco-2A cells. In contrast, gp15 was present on the entire surface of sporozoites as well as merozoites. These results suggest that these two proteins are differentially localized in invasive stages of the parasite.

Other embodiments are within the following claims.

What is claimed is:

1. An isolated polypeptide comprising at least 25 contiguous amino acids of SEQ ID NO:2 or SEQ ID NO:5, wherein the at least 25 contiguous amino acids of SEQ ID NO:2 or SEQ ID NO:5 comprises a polyserine domain consisting of 19 contiguous serine residues and wherein said polypeptide modulates the ability of *C. parvum* sporozoites to attach and invade a host cell.

2. The polypeptide of claim 1, wherein the polypeptide comprises 50 contiguous amino acids of SEQ ID NO:2 or SEQ ID NO:5, wherein the 50 contiguous amino acids of SEQ ID NO:2 or SEQ ID NO:5 comprises a polyserine domain consisting of 19 contiguous serine residues and wherein said polypeptide modulates the ability of *C. parvum* sporozoites to attach and invade a host cell.

* * * * *

UNITED STATES PATENT AND TRADEMARK OFFICE
CERTIFICATE OF CORRECTION

PATENT NO.     : 6,657,045 B1
DATED          : December 2, 2003
INVENTOR(S)    : David Hamer et al.

It is certified that error appears in the above-identified patent and that said Letters Patent is hereby corrected as shown below:

Title page,
Item [56], References Cited, OTHER PUBLICATIONS,
"Verdon *et al.*" reference, replace "1672," with -- 1272 --, and "Ward *et al*" reference, replace "Parqstoil" with -- *Parasitol.* --.

Signed and Sealed this

Twenty-seventh Day of July, 2004

JON W. DUDAS
*Acting Director of the United States Patent and Trademark Office*